US011612637B2

(12) United States Patent
Thai et al.

(10) Patent No.: US 11,612,637 B2
(45) Date of Patent: Mar. 28, 2023

(54) COMPOSITIONS AND METHODS FOR TREATING DIABETES, HYPERTENSION AND HYPERCHOLESTEROLEMIA

(71) Applicant: IMAGINE PHARMA LLC, Devon, PA (US)

(72) Inventors: Ngoc Thai, Pittsburgh, PA (US); Jonathan Pollett, Pittsburgh, PA (US)

(73) Assignee: IMAGINE PHARMA LLC, Pittsburgh, PA (US)

( * ) Notice: Subject to any disclaimer, the term of this patent is extended or adjusted under 35 U.S.C. 154(b) by 0 days.

(21) Appl. No.: 16/931,682

(22) Filed: Jul. 17, 2020

(65) Prior Publication Data

US 2021/0000915 A1    Jan. 7, 2021

Related U.S. Application Data

(63) Continuation-in-part of application No. 16/455,878, filed on Jun. 28, 2019, now Pat. No. 10,751,384.

(51) Int. Cl.
*A61K 38/03* (2006.01)
*A61K 38/17* (2006.01)
*A61P 3/10* (2006.01)

(52) U.S. Cl.
CPC ............... *A61K 38/17* (2013.01); *A61P 3/10* (2018.01)

(58) Field of Classification Search
None
See application file for complete search history.

(56) References Cited

U.S. PATENT DOCUMENTS

2010/0221753 A1\*  9/2010  Stearns ............. C07K 14/4705
435/7.21

OTHER PUBLICATIONS

Guo et al. (Mol. BioSyst. vol. 7, pp. 2286-2295, 2011).\*

\* cited by examiner

*Primary Examiner* — Richard G Hutson

(57) ABSTRACT

The present invention provides a pharmaceutical formulation comprising a therapeutically effective amount of a polypeptide corresponding to SEQ ID No. 2 and uses thereof for treating at least one of diabetes, hyperglycemia, hypercholesterolemia, and hypertension in a subject.

4 Claims, 20 Drawing Sheets

Specification includes a Sequence Listing.

COMPOSITIONS AND METHODS FOR TREATING DIABETES, HYPERTENSION AND HYPERCHOLESTEROLEMIA

CROSS REFERENCE TO RELATED APPLICATIONS

This application is a continuation-in-part of U.S. patent application Ser. No. 16/455,878 filed Jun. 28, 2019, which in turn claims priority to U.S. patent application Ser. No. 15/811,060, filed Nov. 13, 2017, which in turn claims priority to U.S. provisional application No. 62/421,32, filed on Nov. 13, 2016, the contents each of which are incorporated herein by reference, in their entireties.

BACKGROUND OF THE INVENTION

When left uncontrolled, diabetes mellitus, or simply diabetes, results in hyperglycemia, or high blood sugar. Over time, hyperglycemia leads to serious damage to many of the body's systems, especially the nerves and blood vessels. There are multiple variants of diabetes. In Type 1 diabetes, the pancreas produces little to no insulin. Treatment for Type 1 diabetics requires insulin injections. In the most common type of diabetes, Type 2 diabetes, the pancreas does not produce a sufficient amount of insulin, or the insulin produced is less effective due to cellular resistance, or both. The World Health Organization provides that Type 2 represents 90% of the cases of diabetes worldwide. Treatment for Type 2 diabetes includes healthy eating and physical activity, as well as medications and insulin therapy.

Complications of the chronic hyperglycemia of diabetes include endothelial damage, proliferative retinopathy, neuropathy, nephropathy, hypertension and ischemic heart disease. Diabetes is one of the leading causes of heart disease, stroke, kidney failure, blindness, and limb amputations and as such it is a drain on the economies of all industrial countries.

Often in cases of Type 2 diabetes, pharmacological intervention is necessary for treatment. There are many types of approved medications for Type 2 diabetes, such as sulfonylureas, dipeptidyl peptidase IV (DPP-IV) inhibitors, meglitinides, biguanides, thiazolidinediones, and alpha-glucosidase inhibitors. However, these drugs produce unwanted side effects, including upset stomach, hypoglycemia, weight gain, liver problems, skin rash, headache, and respiratory infection. Further, these medications are often used together as a combination therapy in order to be more effective. However, the use of multiple pharmaceuticals increases the likelihood of unwanted side effects. Nearly 50% of Type 2 diabetic patients eventually require administration of insulin.

Insulin administration remains to be the only treatment option for Type 1 diabetes. Furthermore, the treatment of Type I diabetes by insulin cannot avoid the long-term complications induced by daily cycles of hyperglycemia and hypoglycemia, due to the difficulty of determining the exact insulin dosage required in changing physiological conditions.

Hypertension, high cholesterol and hyperglycemia are often present in individuals with both types of diabetes, particularly Type 2 diabetes. The combination of hypertension, high cholesterol and diabetes significantly increases the risk of a heart attack or stroke. Presently, the drugs used to treat these three conditions, (hypertension, high cholesterol and diabetes), have side effects to varying degrees. It would therefore be useful to have a therapeutic composition which lowers blood glucose also modulates blood pressure and cholesterol, without side effects seen in the presently available drugs. Such a composition would have utility in the treatment of hypertension, cholesterol, along with diabetes.

SUMMARY OF THE INVENTION

The present invention relates to novel pharmaceutical compositions and methods for treating clinical diseases, including those associated with high blood pressure and elevated blood glucose level (hyperglycemia), such as: diabetes, stroke, peripheral vascular disease, pulmonary hypertension, metabolic syndrome, hypercholesterolemia and atherosclerosis.

Unexpectedly, it has been discovered that a polypeptide corresponding in sequence homology to an active region of a 40 s ribosomal protein S2, ("RPS2") was beneficial as a therapeutic for oral and iv administration, as evidenced by its ability to facilitate a reduction in blood glucose levels, a reduction in insulin resistance, a reduction in hepatic glucose production, a reduction in glucagon levels, a reduction in blood pressure (systolic and diastolic levels), and a reduction in blood cholesterol levels.

Provided herein are methods and compositions involving pharmaceutical compositions comprising RPS2 polypeptide, RPS2 peptide analogues, and/or mixtures thereof. In one embodiment, a RPS2 polypeptide comprises an amino acid sequence set forth in SEQ ID NO: 1. In another embodiment, the RPS2 polypeptide comprises an amino acid sequence having at least 50% sequence identity to the amino acid sequence set forth in SEQ ID NO: 1. In yet another embodiment, the RPS2 polypeptide has at least 50%, 55%, 60%, 65%, 70%, 75%, 80%, 85%, 90%, 95%, 98% or 99% sequence identity to the amino acid sequence set forth in SEQ ID NO: 1.

In one embodiment, a RPS2 polypeptide comprises an amino acid sequence set forth in SEQ ID NO: 2. In another embodiment, the RPS2 polypeptide comprises an amino acid sequence having at least 50% sequence identity to the amino acid sequence set forth in SEQ ID NO: 2. In yet another embodiment, the RPS2 polypeptide has at least 50%, 55%, 60%, 65%, 70%, 75%, 80%, 85%, 90%, 95%, 98% or 99% sequence identity to the amino acid sequence set forth in SEQ ID NO: 2.

In one embodiment, a RPS2 polypeptide comprises an amino acid sequence set forth in SEQ ID NO: 3. In another embodiment, the RPS2 polypeptide comprises an amino acid sequence having at least 50% sequence identity to the amino acid sequence set forth in SEQ ID NO: 3. In yet another embodiment, the RPS2 polypeptide has at least 50%, 55%, 60%, 65%, 70%, 75%, 80%, 85%, 90%, 95%, 98% or 99% sequence identity to the amino acid sequence set forth in SEQ ID NO: 3.

In a first aspect, the present invention provides an isolated polypeptide that comprises a 40 s ribosomal protein S2 (RPS2) or a fragment thereof or an analog thereto comprising an amino acid sequence having at least 50% sequence identity to the amino acid sequence set forth in SEQ ID NO: 1, 2, 3 or 4. In one embodiment, the present invention provides an isolated polypeptide that consists of a 40 s ribosomal protein S2 (RPS2) or a fragment thereof comprising an amino acid sequence having at least 50% sequence identity to the amino acid sequence set forth in SEQ ID NO: 1, 2, 3 or 4.

In one embodiment, the present invention provides an isolated polypeptide that comprises or consists of a 40 s ribosomal protein S2 (RPS2) comprising an amino acid sequence having at least 50% sequence identity to the amino acid sequence set forth in SEQ ID NO: 1. In one embodiment, the present invention provides an isolated polypeptide that comprises or consists of a 40 s ribosomal protein S2 (RPS2) fragment comprising an amino acid sequence having at least 50% sequence identity to the amino acid sequence set forth in SEQ ID NO: 2. In one embodiment, the present invention provides an isolated polypeptide that comprises or consists of a 40 s ribosomal protein S2 (RPS2) fragment comprising an amino acid sequence having at least 50% sequence identity to the amino acid sequence set forth in SEQ ID NO: 3. In one embodiment, the present invention provides an isolated polypeptide that comprises or consists of a 40 s ribosomal protein S2 (RPS2) fragment comprising an amino acid sequence having at least 50% sequence identity to the amino acid sequence set forth in SEQ ID NO: 4.

In one embodiment, the RPS2 or fragment thereof has at least 55%, 60%, 65%, 70%, 75%, 80%, 85%, 90%, 95%, 98% or 99% sequence identity to the amino acid sequence set forth in SEQ ID NO: 1, 2, 3 or 4. In one embodiment, the RPS2 has at least 55%, 60%, 65%, 70%, 75%, 80%, 85%, 90%, 95%, 98% or 99% A sequence identity to the amino acid sequence set forth in SEQ ID NO: 1. In one embodiment, the RPS2 fragment has at least 55%, 60%, 65%, 70%, 75%, 80%, 85%, 90%, 95%, 98% or 99% sequence identity to the amino acid sequence set forth in SEQ ID NO: 2. In one embodiment, the RPS2 fragment has at least 55%, 60%, 65%, 70%, 75%, 80%, 85%, 90%, 95%, 98% or 99% sequence identity to the amino acid sequence set forth in SEQ ID NO: 3. In one embodiment, the RPS2 fragment has at least 55%, 60%, 65%, 70%, 75%, 80%, 85%, 90%, 95%, 98% or 99% sequence identity to the amino acid sequence set forth in SEQ ID NO: 4.

In one embodiment, the RPS2 or fragment thereof comprises the amino acid sequence set forth in SEQ ID NO: 1, 2, 3 or 4. In one embodiment, the RPS2 comprises the amino acid sequence set forth in SEQ ID NO: 1. In one embodiment, the RPS2 fragment comprises the amino acid sequence set forth in SEQ ID NO: 2. In one embodiment, the RPS2 fragment comprises the amino acid sequence set forth in SEQ ID NO: 3. In one embodiment, the RPS2 fragment comprises the amino acid sequence set forth in SEQ ID NO: 4.

In one embodiment, the RPS2 or fragment thereof consists of the amino acid sequence set forth in SEQ ID NO: 1, 2, 3 or 4. In one embodiment, the RPS2 consists of the amino acid sequence set forth in SEQ ID NO: 1. In one embodiment, the RPS2 fragment consists of the amino acid sequence set forth in SEQ ID NO: 2. In one embodiment, the RPS2 fragment consists of the amino acid sequence set forth in SEQ ID NO: 3. In one embodiment, the RPS2 fragment consists of the amino acid sequence set forth in SEQ ID NO: 4.

In a second aspect, the invention provides a formulation comprising at least one polypeptide according to the invention. The at least one polypeptide according to the invention may be at least one polypeptide according to the first aspect.

In an embodiment, the formulation is an oral pharmaceutical formulation. In an embodiment, the formulation is a pharmaceutical parenteral formulation. In an embodiment, the formulation is a pharmaceutical topical formulation.

In an embodiment, the formulation comprises one or more pharmaceutically acceptable carrier(s) and/or one or more pharmaceutically acceptable diluent(s) and/or one or more pharmaceutically acceptable excipient(s). The formulation may comprise one or more pharmaceutically acceptable carrier(s). The formulation may comprise one or more pharmaceutically acceptable diluent(s). The formulation may comprise one or more pharmaceutically acceptable excipient(s).

In an embodiment, the formulation is an aqueous pharmaceutical formulation. The peptide may be present at a concentration of 0.05 to 5 µg/L in the aqueous pharmaceutical formulation. For example, the peptide may be present at a concentration of 0.08 to 3 µg/L or may be present at 0.1 to 1 µg/L. The peptide may be present at a concentration of at least 0.05 µg/L, for example at least 0.7, 0.1 or 0.15 µg/L. The peptide may be present at a concentration of not more than 5 µg/L, for example not more than 4, 3 or 2 µg/L (e.g. not more than 1 µg/L). The aqueous pharmaceutical formulation may comprise a buffer. The buffer may have a pH of from about 7 to about 8, for example the buffer may have a pH of from about 7.2 to about 7.6, e.g. the buffer may have a physiological pH (a pH of about 7.4, e.g. a pH of from 7.3 to 7.5). The buffer may be phosphate buffered saline.

In a third aspect, the invention provides a medicament comprising a polypeptide of the invention or a formulation of the invention. The polypeptide of the invention may be at least one polypeptide of the first aspect. The formulation of the invention may be a formulation of the second aspect.

In a fourth aspect, the invention provides a polypeptide of the invention or formulation of the invention for use in a method of treating a disease. The polypeptide of the invention may be at least one polypeptide of the first aspect. The formulation of the invention may be a formulation of the second aspect. The disease may be at least one of Type 1 and/or Type 2 diabetes, hyperglycemia, hypercholesterolemia, hypertension and metabolic syndrome. The disease may be Type 1 and/or Type 2 diabetes. The disease may be hyperglycemia. The disease may be hypercholesterolemia. The disease may be hypertension. The disease may be metabolic syndrome.

In a fifth aspect, the invention provides a polypeptide of the invention or formulation of the invention for use in a method of treating Type 1 and/or Type 2 diabetes. The polypeptide of the invention may be at least one polypeptide of the first aspect. The formulation of the invention may be a formulation of the second aspect. The use may provide a reduction in hepatic glucose production, and/or a reduction in cholesterol levels, and/or a reduction in glucagon levels, and/or a reduction in blood pressure. The use may provide a reduction in hepatic glucose production. The use may provide a reduction in cholesterol levels. The use may provide a reduction in glucagon levels. The use may provide a reduction in blood pressure.

In a sixth aspect, the invention provides use of at least one polypeptide according to the invention for the manufacture of a medicament for the treatment of Type 1 and/or Type 2 diabetes. The polypeptide according to the invention may be at least one polypeptide of the first aspect.

In a seventh aspect, the invention provides use of at least one polypeptide according to the invention for the manufacture of a medicament for the treatment of at least one of hyperglycemia, and/or hypercholesterolemia, and/or hypertension, and/or metabolic syndrome. The polypeptide according to the invention may be at least one polypeptide of the first aspect. The medicament may treat hyperglycemia. The medicament may treat hypercholesterolemia. The medicament may treat hypertension. The medicament may treat metabolic syndrome.

In an eighth aspect, the invention provides a method for treating at least one of diabetes, and/or hyperglycemia, and/or hypercholesterolemia, and/or hypertension in a subject, comprising: administering to the subject a polypeptide of the invention or formulation of the invention. The polypeptide of the invention may be at least one polypeptide of the first aspect. The formulation of the invention may be a formulation of the second aspect. The method may comprise administering an effective amount of said polypeptide or said formulation. The method may treat diabetes (e.g. Type 1 and/or Type 2 diabetes). The method may treat hyperglycemia. The method may treat hypercholesterolemia. The method may treat hypertension.

The present invention provides a pharmaceutical composition comprising a therapeutically effective amount of a RPS2 polypeptide or peptide analog corresponding to one or more of SEQ ID NO(s) 1, 2, 3 or 4, and or more of a pharmaceutically acceptable carrier, and/or one or more of a pharmaceutically acceptable diluent, and/or one or more of a pharmaceutically acceptable excipient. The polypeptide therapeutic of the present invention may be formulated for administration to a subject in need of treatment as an oral formulation, a parenteral formulation, a topical formulation, an aqueous formulation, a solid formulation, a lyophilized formulation, or a trans-dermal formulation.

DETAILED DESCRIPTION OF THE INVENTION

Figure 1:
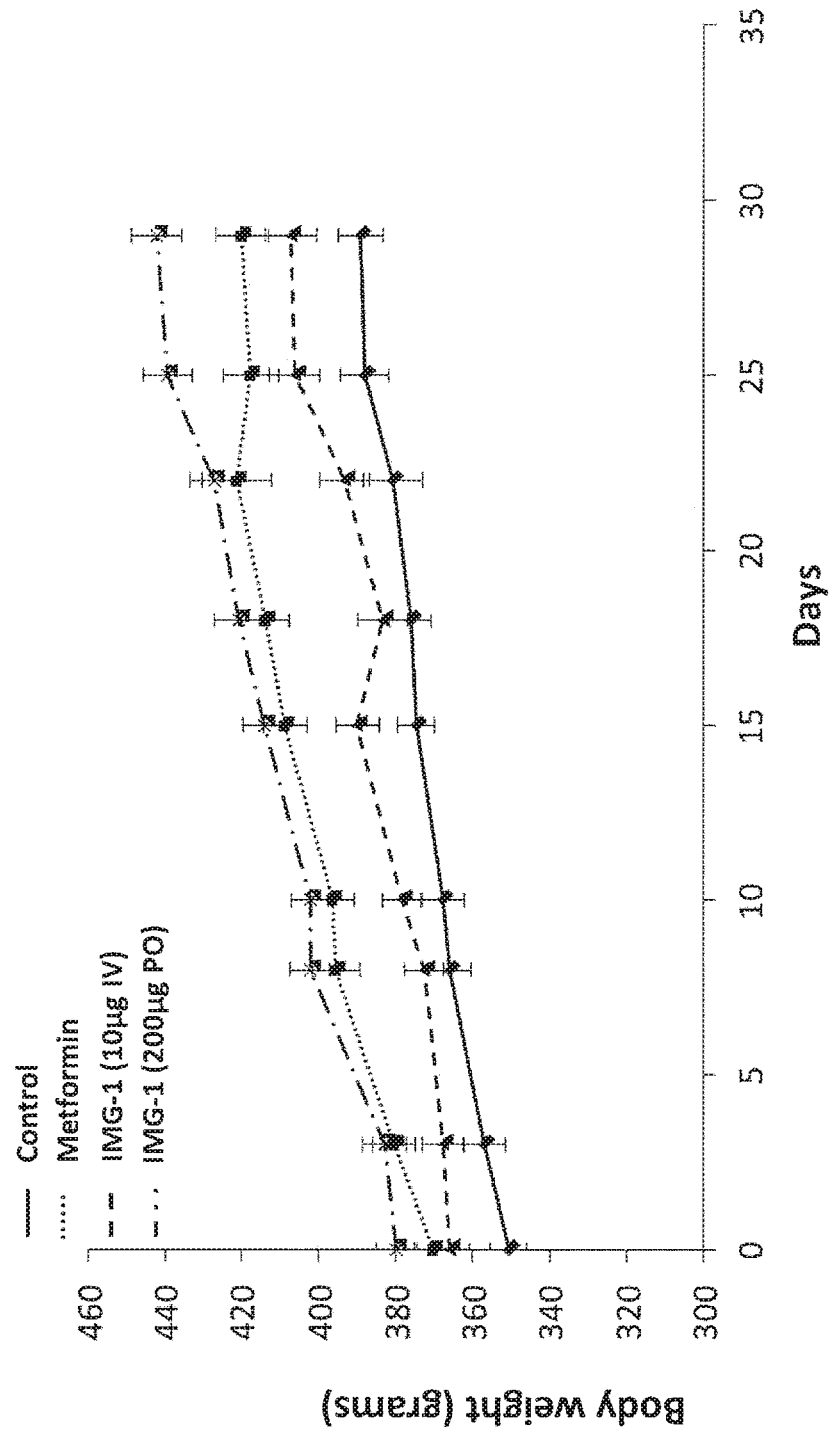
FIG. 1 is a graph showing the relationship between body weight in diabetic animals (the Zucker diabetic rat animal model) treated with metformin and/or IMG-1 administered intravenously (10 µg) and orally (200 µg), showing weight gain was consistent amongst the animals.

The following detailed description is provided to aid those skilled in the art in practicing the present invention, but should not be construed to limit the present invention as modifications and variations in the embodiments disclosed herein may be made by those of ordinary skill in the art without departing from the scope and spirit of the present invention. All publications and other references cited in this application are hereby incorporated by reference in their entirety.

The following terms are used in this disclosure to describe different aspects of the invention. These terms are used for explanation purposes only and are not intended to limit the scope for any aspect of the invention.

As used herein "active ingredient", "active compound", "active component", and/or "active agent" may be used interchangeably and refer to a polypeptide, peptide fragment, or analogue thereof having an amino acid sequence comprising an amino acid sequence of SEQ ID NO. 1; or SEQ ID NO: 2, or SEQ ID NO: 3, SEQ ID NO: 4, or combinations thereof. Formulations of the present invention comprising the active ingredient/compound are collectively referred to as "IMG-1" formulations, without implying any specific dosage or concentration of active compound.

As used herein "effective amount" refers to that amount of the active ingredient/compound, which, when administered to a subject is effective to lower blood glucose levels to less than 200 mg/dl, lower cholesterol to less than 200 mg/dl, and/or lower blood pressure to less than 140/90 mmHg.

As used herein "pharmaceutical formulation", "pharmaceutical composition", "formulation", or "composition" refer (interchangeably) to a liquid (aqueous, gel, or ointment), or a solid form containing an amount of active compound, which is prepared so that it is suitable for administration to a mammal, such as a human or other animal, directly or after reconstitution. If needed, the formulation may contain pharmaceutically acceptable carriers and/or additives. For example, detergents/surfactants (e.g. PEG, Tween (20, 80, etc.), Pluronic), excipients, antioxidants (e.g. ascorbic acid, methionine), coloring agents, flavoring agents, preservatives, stabilizers, buffering agents, chelating agents (e.g. EDTA), suspending agents, isotonizing agents, binders, disintegrants, lubricants, fluidity promoters, and corrigents. The pharmaceutical compositions of the present invention may contain other active ingredients in combination with the RPS2 polypeptide and/or polypeptide analogues described herein.

As used herein, the terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

As used herein, a "therapeutically effective amount" to treat a condition, such as diabetes or hypertension, is an amount of active compound capable of achieving a clinically-relevant end-point in a patient or patient population, such as reduced blood glucose levels in diabetes or reduced blood pressure in hypertension or reduced cholesterol in hypertriglyceridemia or hypercholesterolemia. As non-limiting examples, administration of an effective amount of an IMG-1 composition has been shown in animal studies to lower blood glucose to less than 200 mg/dL (in a diabetes animal model); lower blood pressure to less than 140/90 mmHg; and lower total cholesterol to less than 200 mg/dL.

The present invention provides a pharmaceutical composition for treating one or more diseases in a subject, the diseases comprising one or more of diabetes (Type I or Type 2), hypertension, hypercholesterolemia, vascular disease, or metabolic syndrome. The pharmaceutical compositions comprise a purified or synthetic RPS2 polypeptide or peptide analogue corresponding to one or more of SEQ ID NO 01, SEQ ID NO.: 2, SEQ ID NO: 3, SEQ ID NO: 4, or active regions thereof, in combination with one or more of a pharmaceutically acceptable carrier, diluent or excipient. The pharmaceutical composition may be formulated for oral, parenteral or dermal/topical administration to a subject in need of treatment.

In another embodiment, the present invention provides an aqueous pharmaceutical formulation comprising a purified or synthetic RPS2 peptide, analogue, or active region thereof, a buffer, such as phosphate buffered saline (PBS), wherein the formulation has a pH within the normal physiological range (approximately 7.4) and wherein the RPS2 polypeptide or peptide analogue comprises an amino acid sequence set forth in one or more of SEQ ID NO 01, SEQ ID NO: 2, SEQ ID NO: 3, or SEQ ID NO: 4.

Also provided is a method of preventing, delaying the onset of, or reducing the severity of one or more conditions comprising hyperglycemia, hypertension and/or hypercholesterolemia. The present invention also provides methods and compositions for improving protein expression in cell culture, particularly yeast, bacterial and mammalian cell culture, including media for growing cells for protein expression and cell culture production media optimized for protein expression.

The present invention is also described through examples and experimental results, which are intended as illustrative and not exhaustive, and shall be understood as not being limited thereto.

Surprisingly, it has been discovered that a purified, isolated 40 s ribosomal protein S2 (RPS2), including truncated fragments, exhibits therapeutic benefits when administered to a subject, including: the ability to reduce blood glucose levels; normalize blood glucose levels; lower blood cholesterol levels; reduce and normalize blood pressure levels; decrease hemoglobin A1c levels; decrease glucagon levels; and decrease insulin resistance. By way of reference, 40 s RPS2 is a protein belonging to the S5P family of ribosomal proteins. With respect to humans, the RPS2 gene encodes a ribosomal protein that is a component of the 40S subunit and is located in the cytoplasm.

The RPS2 amino acid sequence does not contain a typical nuclear localization signal. Using deletion mutant analysis and rpS2-β-galactosidase chimeric proteins the putative identify of the nuclear targeting domains in RPS2 was determined. A central domain comprising 72-75 amino acids is necessary and sufficient to target the chimeric β-galactosidase to the nucleus. The nuclear targeting domain shares no significant similarity to already-characterized nuclear localization signals in ribosomal proteins or other nuclear proteins.

The full length RPS2 amino acid sequence is a 293 amino acid sequence designated SEQ ID NO: 1; a truncated C-terminus fragment of SEQ ID NO: 1 is a 159 amino acid fragment and is designated SEQ ID NO: 2; the unconventional nuclear localization signal is a 75 amino acid fragment located between amino acids 161-235 of SEQ ID NO: 1, and is designated SEQ ID NO: 3; an 87 amino acid fragment located between amino acids 135-221 of SEQ ID NO: 1 is designated SEQ ID NO: 4; a truncated N-terminus fragment of SEQ ID NO: 1 is a 134 amino acid fragment and is designated SEQ ID NO: 5.

RPS2 polypeptide of SEQ ID NO: 1 is 94%-100% homologous amongst all animals when compared by sequence analysis performed utilizing the BLAST database (https://blast.ncbi.nlm.nih.gov). The C-terminus region comprised of 159 amino acids of SEQ ID NO: 2 is 99-100% homologous for the Animalia phylum. The 75 amino acid nuclear localization sequence corresponding to SEQ ID NO: 3 shares 99-100% homology between all animals and bacteria. Whereas animal/bacteria protein sequence is on average 98-100% homologous, homology to plants can be as low as 77% homologous.

The invention includes proteins and peptides having an identity of at least 75%, at least 80%, at least 85%, at least 90%, at least 95% with a protein or peptide of the disclosure, e.g. 96% or more, 97% or more, 98% or more or 99% or more; such proteins may have the activity of the corresponding protein or peptide of the disclosure.

An RPS2 C-terminus fragment of the present invention is a 159 amino acid fragment of ~18 kDa. The C-terminus fragment is shown below and designated SEQ ID NO: 2:

GHVGLGVKCSKEVATAIRGAIILAKLSIVPVRRGYWGNKIGKPHT

VPCKVTGRCGSVLVRLIPAPRGTGIVSAPVPKKLLMMAGIDDCYT

SARGCTATLGNFAKATFDAISKTYSYLTPDLWKETVFTKSPYQEF

TDHLVKTHTRVSVQRTQAPAVATT

An RPS2 C-terminus fragment of the present invention is a 159 amino acid fragment of ~18 kDa. The C-terminus fragment is shown below and designated SEQ ID NO: 2:

GHVGLGVKCSKEVATAIRGAIILAKLIVPVRRGYWGNKIGKPHTVPCKVT

GRCGSVLVRLIPAPRGTGIVSAPVPKKLLMMAGIDDCYTSARGCTATLGN

FAKATFDAISKTYSYLTPDLWKETVFTKSPYQEFTDHLVKTHTRVSVQRT

QAPAVATT

A 75 amino acid nuclear localization signal of the present invention (corresponding to a sequence between amino acids 161-235 of SEQ ID NO: 1) is shown below and designated SEQ ID NO: 3:

SIVPVRRGYWGNKIGKPHTVPCKVTGRCGSVLVRLIPAPRGTGIVSAPVP

KKLLMMAGIDDCYTSARGCTATLGN

An 87 amino acid sequence corresponding to a portion of the nuclear localization signal near the N-terminus between amino acids 135-221 of SEQ ID NO: 1 is shown below and designated SEQ ID NO: 4

GHVGLGVKCSKEVATAIRGAIILAKLSIVPVRRGYWGNKIGKPHTVPCKV

TGRCGSVLVRLIPAPRGTGIVSAPVPKKLLMMAGIDD

An RPS2 N-terminus fragment of the present invention is a fragment of ≈13 kDa and designated SEQ ID NO: 5:

MADDAGAAGGPGGPGGPGMGNRGGFRGGFGSGIRGRGRGRGRGRGRGA

RGGKAEDKEWMPVTKLGRLVKDMKIKSLEEIYLFSLPIKESEIIDFFLGA

SLKDEVLKIMPVQKQTRAGQRTRFKAFVAIGDYN

Amino acids contained in the amino acid sequences in the present invention may be post-translationally modified according to methods known in the art. For example, the modification of an N-terminal glutamine (Gln) residue into a pyroglutamic acid (pGlu) residue by pyroglutamylation is well-known to those skilled in the art. Naturally, such post-translationally modified amino acids are included in the amino acid sequences and within the scope of the present invention.

Purification of RPS2 and RPS2 Expression In Vitro

The RPS2 gene encoding the human 40S ribosomal protein S2, and various peptide portions, was subcloned into a pMAL-5 vector (New England Biolabs). The RPS2 gene was amplified using a forward primer (sequence: atggcg-gatgacgccggtgc) and a reverse primer (sequence: ctatgttgtagccacagctgg) and the resulting PCR fragment was phosphorylated and purified from low melt agarose. The resulting sequence was ligated into the pMAL-5 vector, and following ligation and incubation, spread on LB plates containing 100 µg/ml ampicillin and incubated overnight at 37° C. to generate transformant for in vivo protein production.

Generation of RPS2 Protein In Vivo

The RPS2 transformant was inoculated into 5 ml of broth and grown to 2×108 cells/ml. This culture was used to inoculate a 200 mL LB amp 0.2% glucose to an A600 of around 0.5. The culture was then induced by adding ITPG (isopropylthio-β-galactoside) to a final concentration of 0.3 mM and grown for an additional 4 h at 30° C. The cells were then centrifuged and re-suspended in 25 ml column buffer per liter of culture. The cells were lysed by freeze-thaw followed by passaging through a 20-gauge needle. The lysed cells were centrifuged, and the supernatant diluted by adding 125 ml cold CB for every 25 ml crude extract. The diluted crude extract was added to a 15 ml amylose column and washed with 12 column volumes of CB. The protein was eluted with CB and maltose (10 mM). The resulting elution was incubated with 1 µL Factor Xa diluted to 200 µg/ml for 4 hours at room temperature. The fusion protein cleavage mixture was dialyzed at pH 8.0 and the amylase columns were washed with buffer and the fusion protein cleavage mixture was loaded onto a column. The flow-through was collected and the amount of isolated protein was determined by bicinchoninic acid assay (BSA) assay and the amount of protein was assessed via ELISA.

For in vivo animal studies, a purified RPS2 protein corresponding to SEQ ID NO: 1 in solution following column purification was diluted with PBS to the desired concentrations (depending on oral or iv administration). The subsequent solution was then filtered through a 0.22 urn filter to filter-sterilize the formulation for administration to animal subjects, as described in the Examples.

Similar studies were carried out with the gene for bacterial RPS2 resulting in similar results in vivo as compared to human RPS2. Various studies were carried out to test the safety and efficacy of isolated RPS2 polypeptide and peptide fragments as a therapeutic, including testing of IMG-1 formulations in a diabetic animal model, as well as toxicology studies in a control animal model. The studies performed and results obtained are presented herein as Examples, along with accompany Figures.

Example 1: Type 2 Diabetes Animal Model

The Zucker Diabetic Fatty (ZDF) strain of rat is widely known and commonly used to study Type 2 Diabetes associated with obesity, as well as hypertension and high cholesterol. The ZDF strain is an inbred rat model of early-onset diabetes in which all of the fa/fa male rats develop diabetes at 10 to 12 weeks of age when fed a special diet of Purina 5008 (Charles River Laboratories International, Inc., Wilmington, Mass., USA). The phenotype is homogeneous, mainly due to the fact that the strain is genetically inbred and that a special diet is provided.

Zucker Diabetic Fatty (ZDF) rats were fed a special diet of Purina 5008 (Charles River Laboratories International, Inc.) to increase their body weight. Prior to the study the animals blood glucose levels were assessed; only rats who had blood glucose levels greater than 200 mg/dl were used in the study. The animals were randomly divided into 4 groups, untreated (n=7), once-daily metformin (200 mg/kg, n=7), 10 µg once-daily IMG-1 intravenously (IV, n=8) and once-daily 200 µg IMG-1 orally administered (PO, n=9). The animals were maintained on this diet for 35 days with their weight measured twice a week. After 35 days the animals were sacrificed. FIG. 1 shows the distribution of body weight (grams) per group, measured over a thirty-day period.

Figure 2:
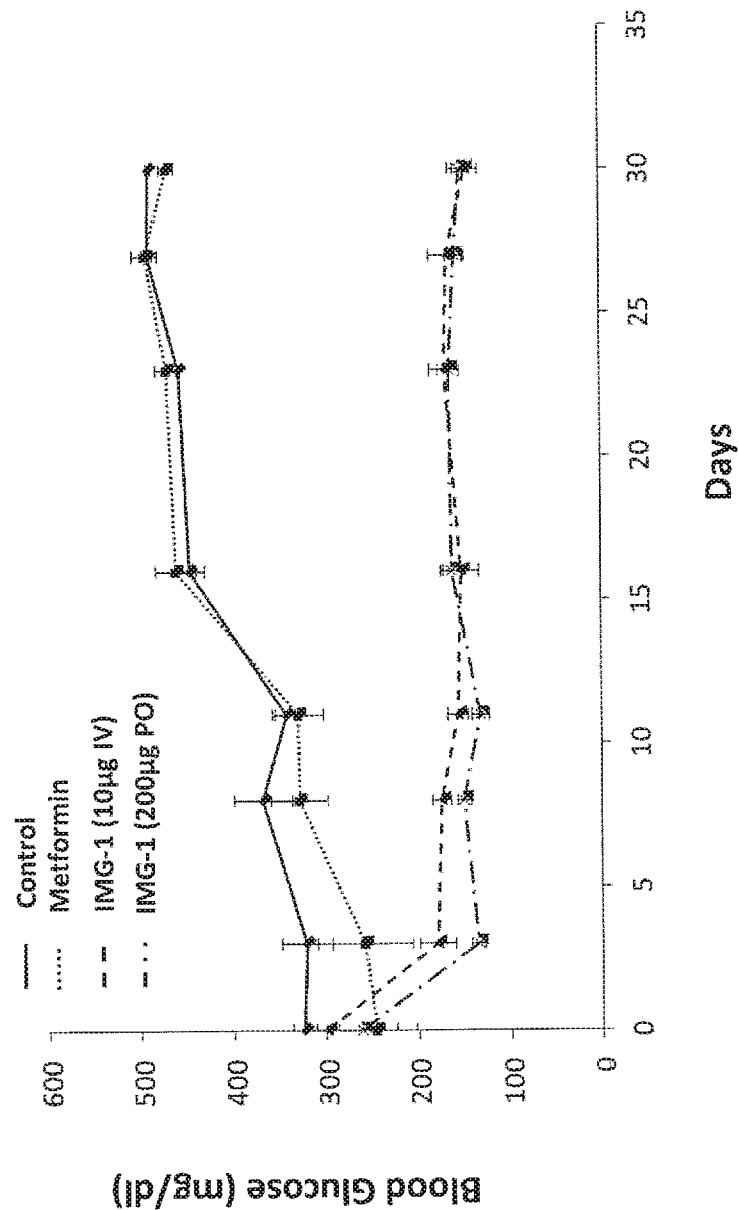
FIG. 2 is a graph showing that treatment of diabetic animals with IMG-1 formulations (oral and IV) resulted in normalized blood glucose levels, compared to control and metformin.

Fasting blood glucose (FBG) levels were assessed in the ZDF throughout the experiment using an Accutrend Plus System. ZDF rats treated with IMG-1 showed a marked decrease in blood glucose levels as early as 3 days post treatment regardless of the modality administered, (average FBG levels of 179 mg/dl for IV administered IMG-1 and 135 mg/dl PO administrated IMG-1 vs FBG levels of 281 mg/dl and 258 mg/dl in the untreated and metformin treated groups respectively), with all IMG-1 treated animals having normal FBG levels (levels below 200 mg/dl) by day 7. Untreated controls and metformin treated animals had significantly elevated FBG levels throughout the study with average levels exceeding 400 mg/dl (481 mg/dl and 468 mg/dl respectively) at the end of the study. FIG. 2 shows that IMG-1 normalizes blood glucose levels in the diabetic animal model; blood glucose levels were lowered in animals treated with IMG-1 versus control and metformin.

Figure 3:
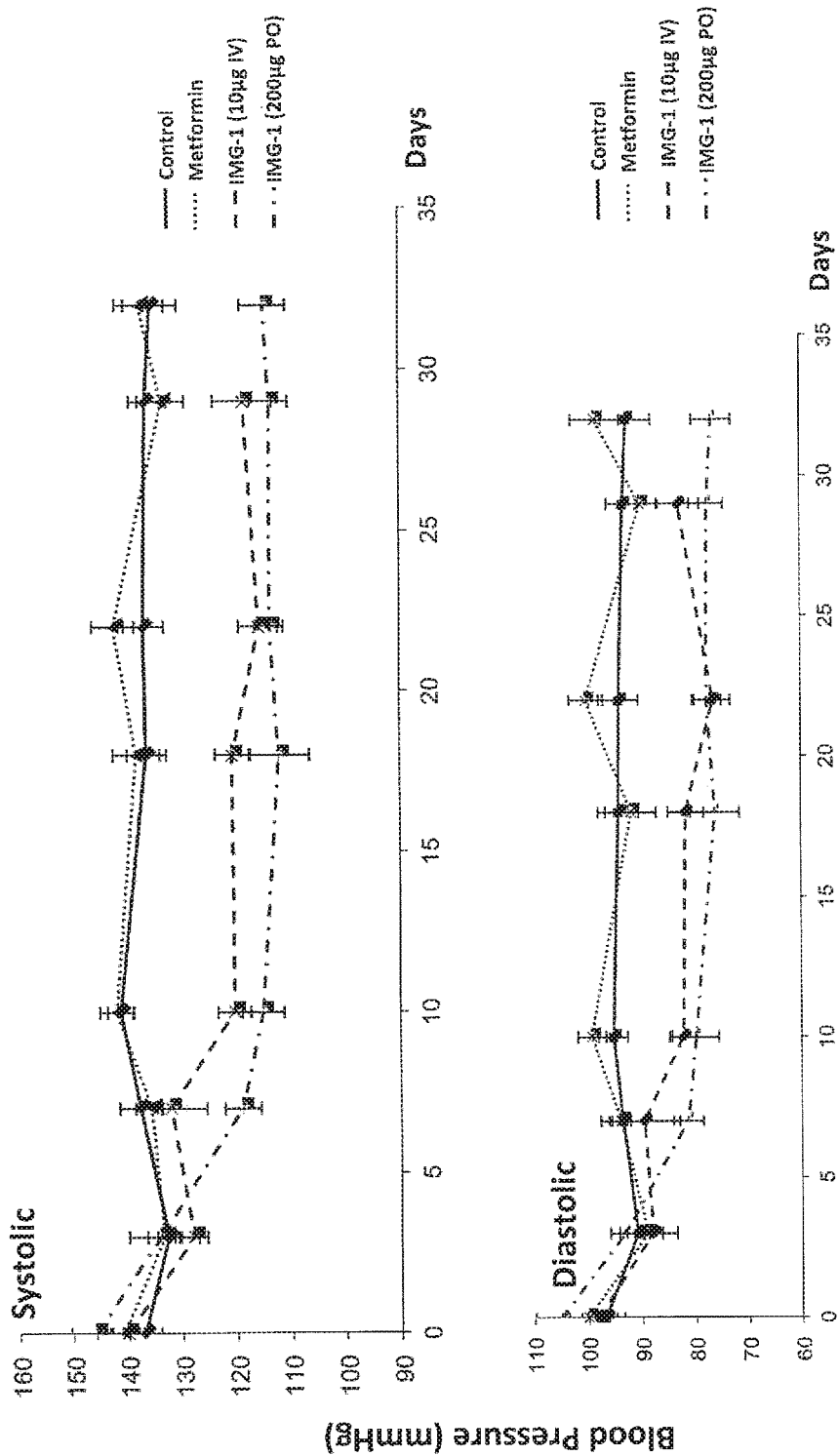
FIG. 3 is a graph showing that treatment of diabetic animals with IMG-1 formulations (oral and IV) resulted in normalized blood pressure (systolic and diastolic) levels, compared to control and metformin.

The blood pressure of the ZDF rats was monitored twice-weekly using a tail cuff blood pressure monitor (CODA, Monitor from Kent Scientific). Within 3 days of treatment rats treated with IMG-1 started exhibiting lower blood pressure and ZDF rats who received IMG-1 orally had normal BP by day 7, while those who received intravenous IMG-1 had normal BP by day 10 (120/82 mmHg and 115/80 mmHg for IV and PO administered IMG-1 respectively). Whereas the untreated and metformin treated ZDF rats had hypertension (>140/90 mmHg, 141/95 mmHg untreated and 142/99 mmHg metformin treated). FIG. 3 shows systolic and diastolic blood pressure levels in animals treated with IMG-1 versus control and metformin; treatment with IMG-1 normalizes blood pressure in the diabetic animal model.

Figure 4:
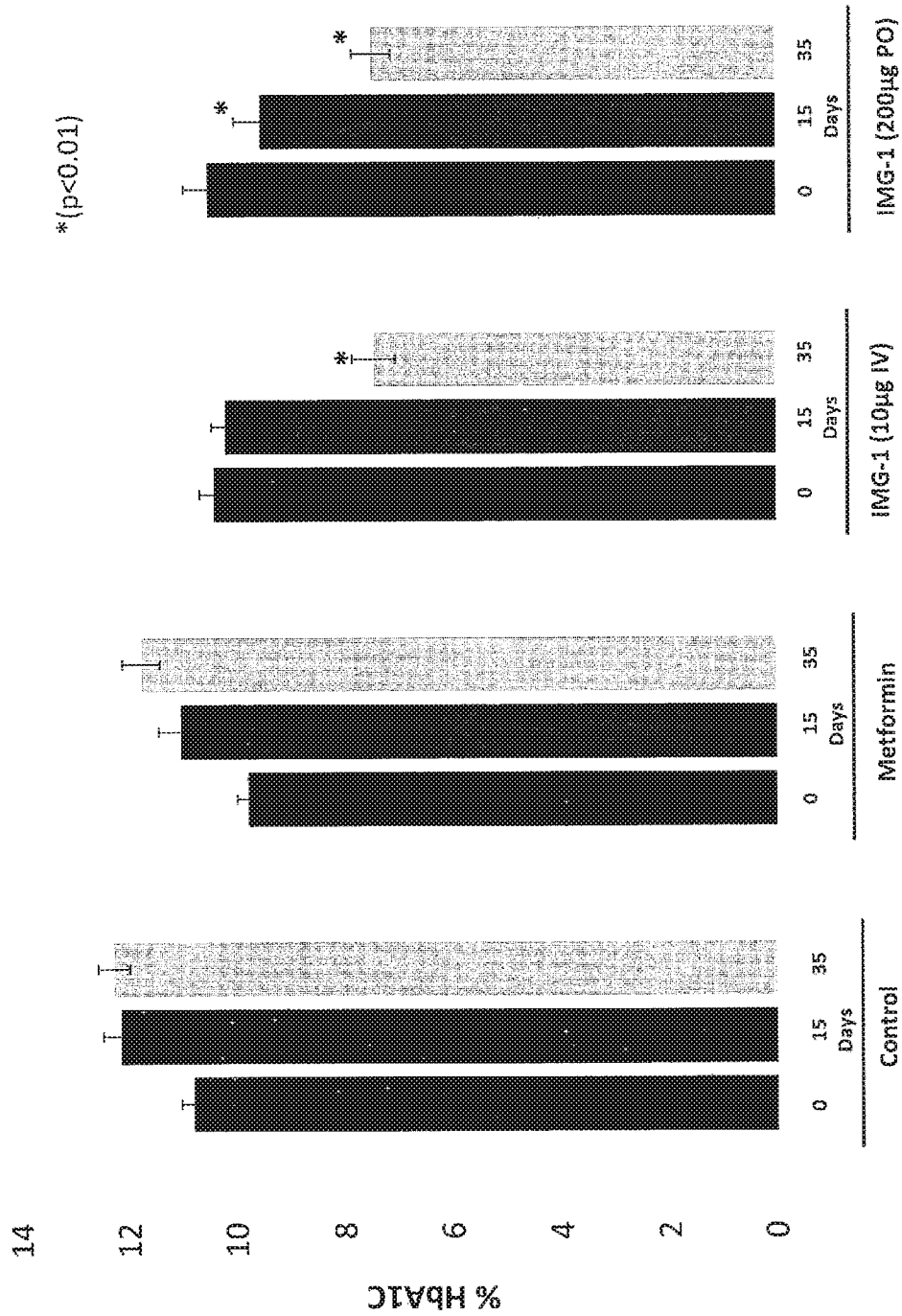
FIG. 4 is a bar graph showing that treatment of diabetic animals with IMG-1 formulations (oral and IV) resulted in decreased HbA1c levels, as compared to control and metformin.

To assess HbA1c levels, blood draws were performed on all animals on days 0, 15 and upon sacrifice on day 35. Bioassays were performed on the harvested blood and sera. Levels of Hemoglobin A1c (HbA1c) were measured in all animals at all three time points. As shown in FIG. 4, the average Hb1Ac levels were not significantly different on day 0 (between 9.7 and 10.8); at day 15 the levels of Hb1Ac were significantly lower in IMG-1 treated groups compared to both untreated and metformin groups (10.2 IV and 9.5 PO vs 12.1 untreated and 11.0 metformin) and by day 35 IMG-1 treated animals had significantly lower levels (7.4 IV and 7.5 PO) than both the untreated and metformin treated animals (12.3 untreated and 11.8 metformin) as well as their own initial starting levels (10.4 IV and 10.5 PO).

Figure 5:
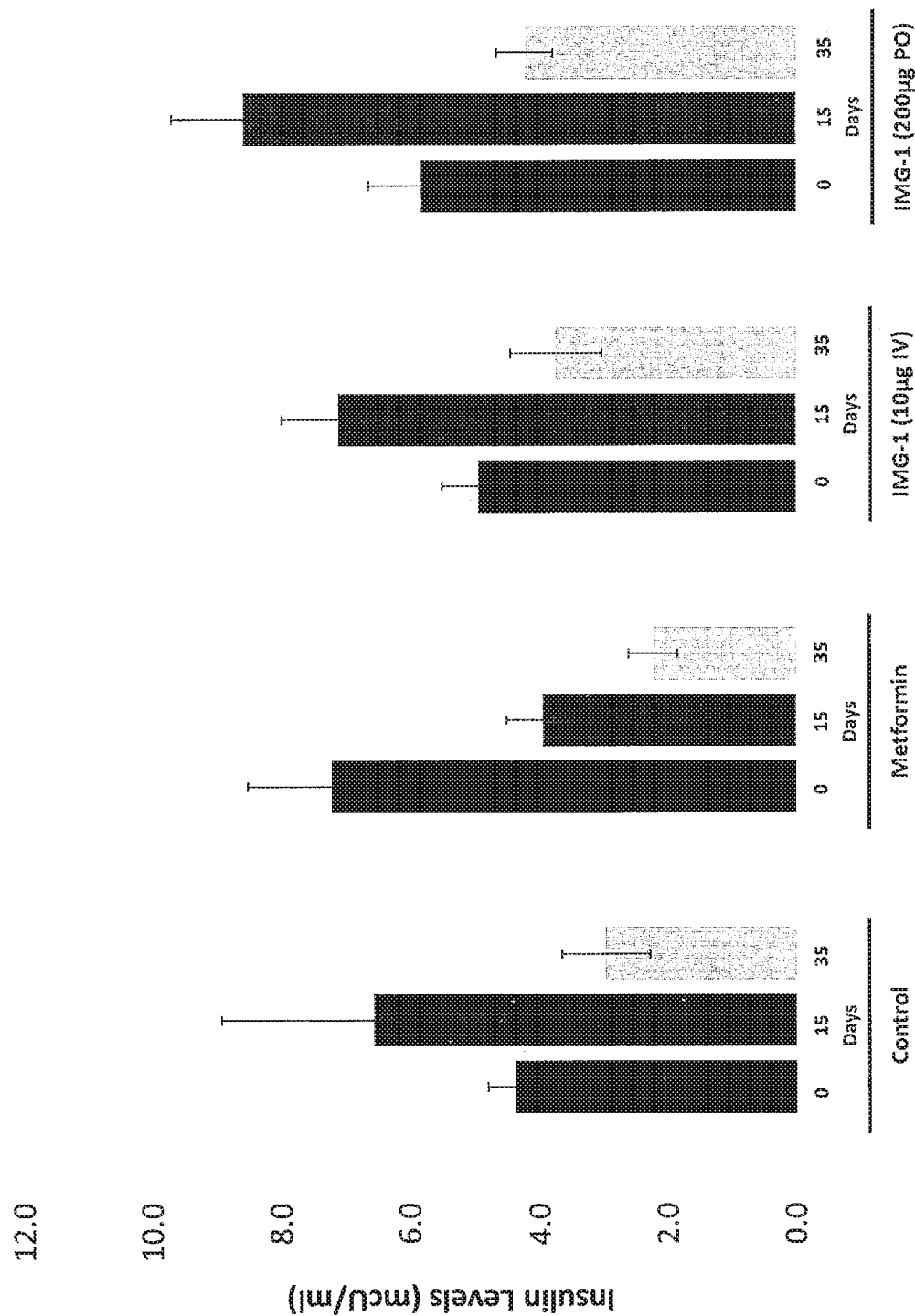
FIG. 5 is a bar graph showing that treatment of diabetic animals with IMG-1 formulations (oral and IV) does not affect insulin levels (mcU/mL).

Along with Hb1Ac levels, insulin levels were measured in all animals at the three time points. As shown in FIG. 5, but unlike Hb1Ac levels shown in FIG. 4 there was no significant difference in insulin levels between untreated and IMG-1 treated groups at any of the three time points. Moreover, the results seen in the control were consistent with the literature.

Figure 6:
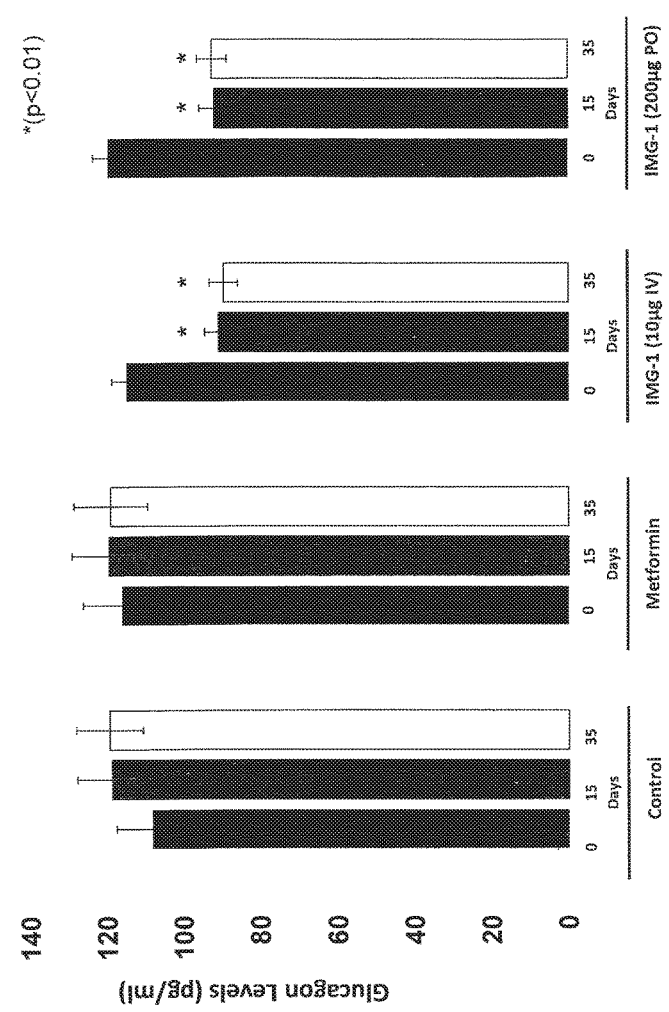
FIG. 6 is a bar graph showing that treatment of diabetic animals with IMG-1 formulations (oral and IV) resulted in decreased glucagon levels, compared to control and metformin.

Though there were no changes in the insulin levels of IMG-1, metformin and control animals, there was a significant decrease in the glucagon levels of both IV and PO IMG-1 treated animals at days 15 (from 115 µg/ml and 119 µg/ml to 90 µg/ml and 92 µg/ml respectively) and 35 (89 µg/ml and 92 µg/ml); control and metformin treated animals had no significant difference in glucagon levels throughout the entire study. FIG. 6 shows IMG-1 decreases glucagon levels in the diabetic animal model; the decrease in glucagon levels as compared to control was consistent between oral and IV administered IMG-1.

Figure 7:
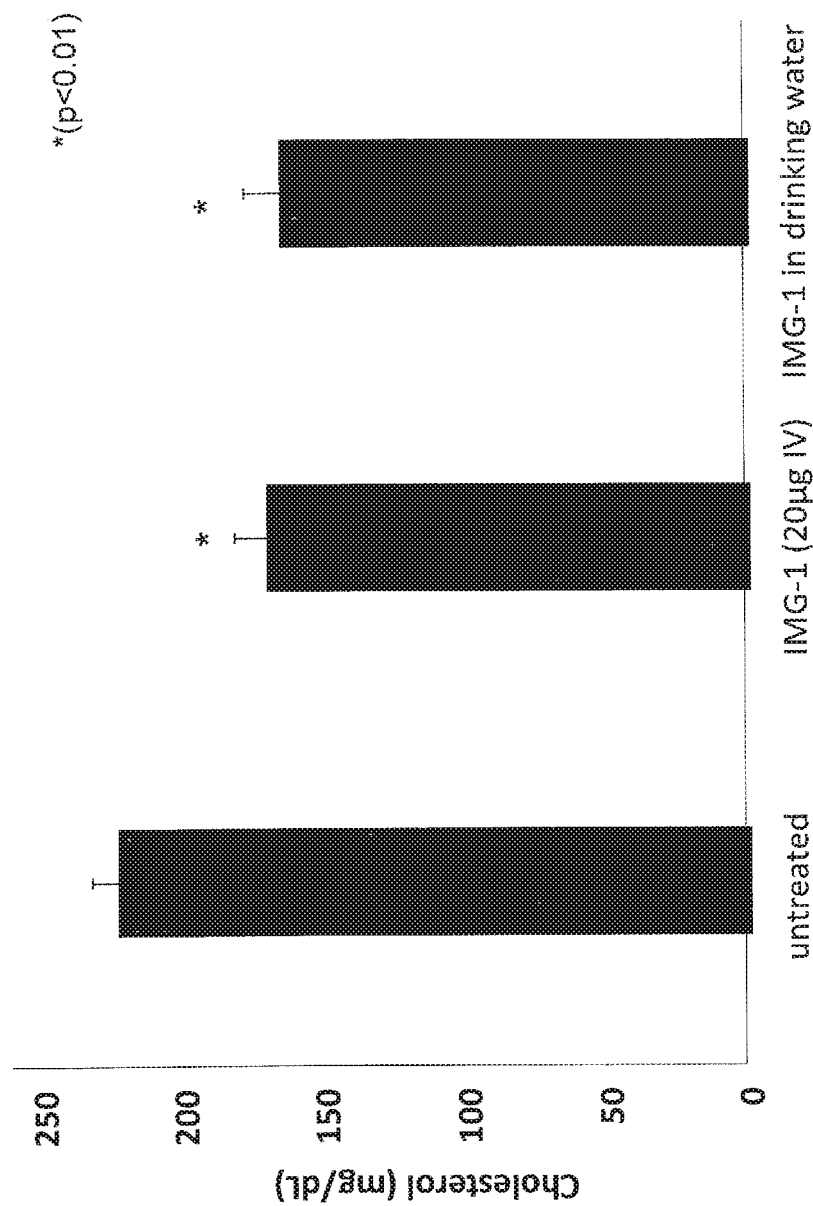
FIG. 7 is a bar graph showing the mean cholesterol levels (mg/dL) as measured from diabetic animals administered IMG-1 (oral and intravenous), were lower as compared to untreated control. Treated animals averaged <170 mg/dL, whereas control measured 224 mg/dL.

The cholesterol levels of ZDF rats were assessed 48 hours following a single dose injection of 20 µg IMG-1, after having continuous access to IMG-1 in the drinking water or untreated (n=4). IMG-1 treated animals had significantly decreased levels of cholesterol compared to the untreated cohort. FIG. 7 shows that IMG-1 decreases cholesterol in the diabetic animal model; untreated animals had a cholesterol level of 224 mg/dL, while IMG-1 treated animals had cholesterol levels of 171 mg/dL (IV) and 156 mg/dL (oral), respectively.

Example 2: Type I Diabetes Animal Model

As IMG-1 was shown to normalize blood glucose levels and decrease HA1C in a Type 2 diabetic animal model, it was ascertained if IMG-1 could affect blood glucose levels in a Type/diabetic animal model. Diabetes can be induced in mice by using streptozotocin (STZ), a compound that has a preferential toxicity toward pancreatic β cells and is a widely used chemical for the induction of experimental diabetes in rodents. STZ is an antibiotic produced by the bacterium *Streptomyces* achromogens and contains a glucose molecule (in deoxy form) that is linked to a highly reactive methyl-nitrosourea moiety that exerts a cytotoxic effects to the pancreatic β cells.

To investigate the efficacy of IMG-1 in a STZ-induced diabetes model 20 male C57BL/6J mice at 3-4 months were administered STZ via IP injection for 5 days, in order to promote development of hyperglycemia. After STZ injection, pre-treatment (baseline) blood glucose levels were measured after a 4-hr fast and used to select mice into 2 study groups: Control Group (placebo, n=7) and IMG-1 Group (n=8/group). The animals were treated for 3 weeks with once daily oral gavage of Control or 33 µg IMG-1 PO. During the treatment phase the fasting blood glucose levels was measured at 2-3-day intervals and the insulin and glucagon levels were measured as well. At eighteen days post-STZ treatment it was shown that fasting blood glucose levels of Control Group animals were elevated from 216 mg/di to 319 mg/dl, and one of the Control Group animals (~14%) had to be euthanized due to failure to thrive.

Figure 8:
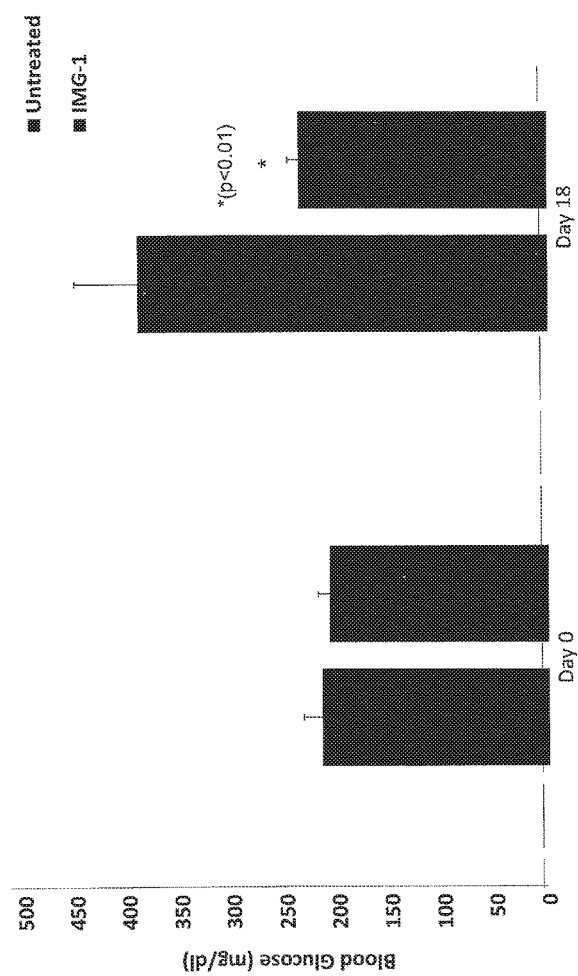
FIG. 8 is a bar graph showing that IMG-1 formulations are effective at lowering blood glucose levels in a Type 1 diabetes animal model, reduction was significant as compared to control (untreated) diabetic-induced animals.

However, the blood glucose levels of the IMG-1 Group saw only a slight increase of glucose level, from 209 mg/dl to 237 mg/dl, and by day 18 it was shown that the IMG-1 Group had significantly lower blood glucose levels than the control animals, as shown in FIG. 8.

Example 3: Toxicology and PK Studies

Figure 9:
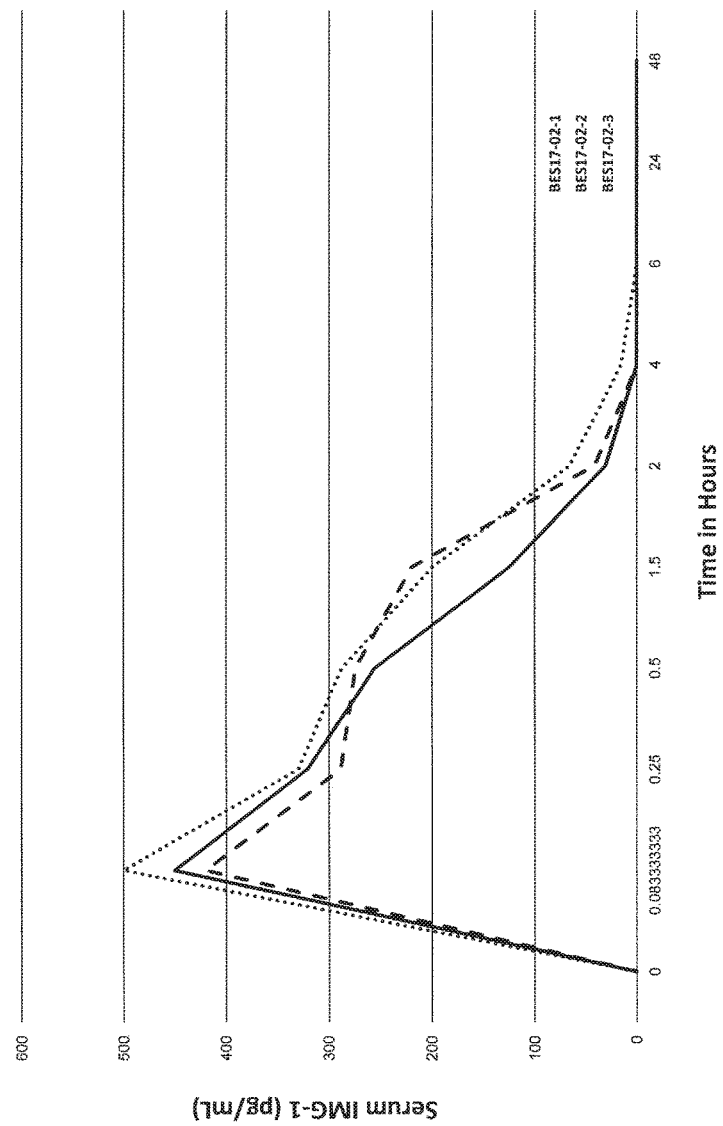
FIG. 9 is a graph showing the clearance of IMG-1 (measured as µg/mL) from serum over a 24-hour period in a Sprague Dawley animal model. Results shown are labeled as BES17-02-1, 2, 2 (indicated three animals).
Figure 10:
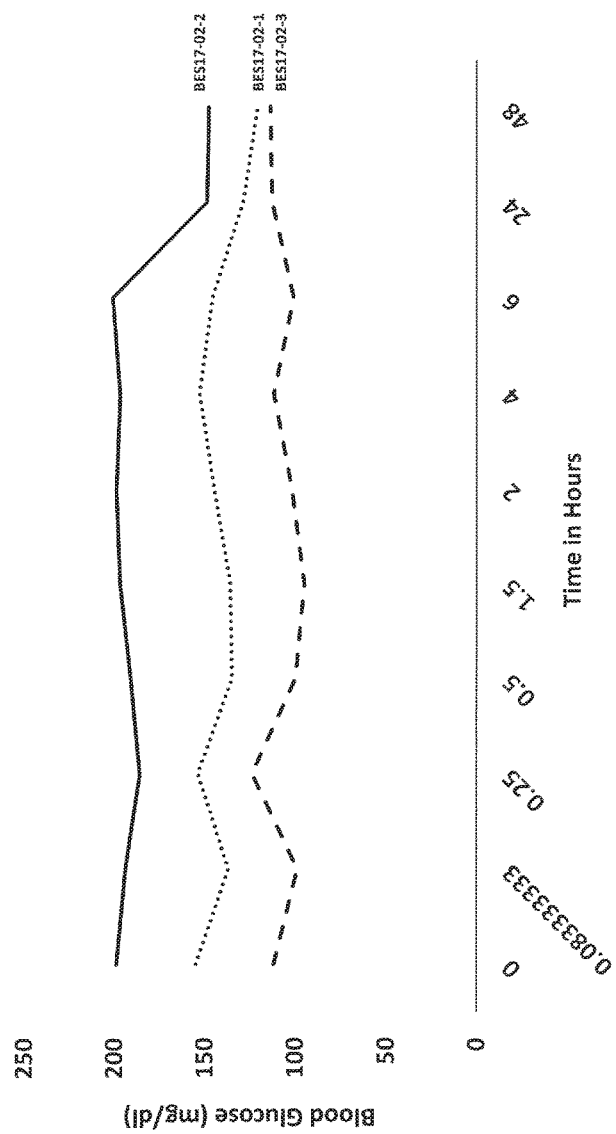
FIG. 10 is a graph showing blood glucose levels in Sprague Dawley animals treated with IMG-1 formulations.

The Sprague Dawley model was utilized to access clearance and toxicology of IMG-1 formulations. Three male Sprague Dawley rats were treated with 20 µg active compound (corresponding to SEQ ID NO: 1) by intravenous administration, followed by blood draws at intervals, specifically: 0, 5 minutes (min), 15 min, 30 min, 60 min, 90 min, 2 hours (h), 4 h, 6 h, 24 h and 48 h post-IMG-1 administration. Active compound was detected in the blood of all three animals up to 2 h post administration, with a third animal displaying detectable levels up to 4 h post treatment, as shown in FIG. 9 by the serum level of IMG-1 active compound (µg/mL) measured over a 6 hour time period. Along with active compound level, blood glucose levels were assessed in the Sprague Dawley model. While IMG-1 administration dramatically decreased blood glucose levels in ZDF rats, a single dose of IMG-1 formulation (20 µg) administered to Sprague Dawley rats did not promote hypoglycemia within 48 h (as shown in FIG. 10) as seen by the blood glucose levels over a 48 hour period in the Sprague Dawley animals.

Figure 11:
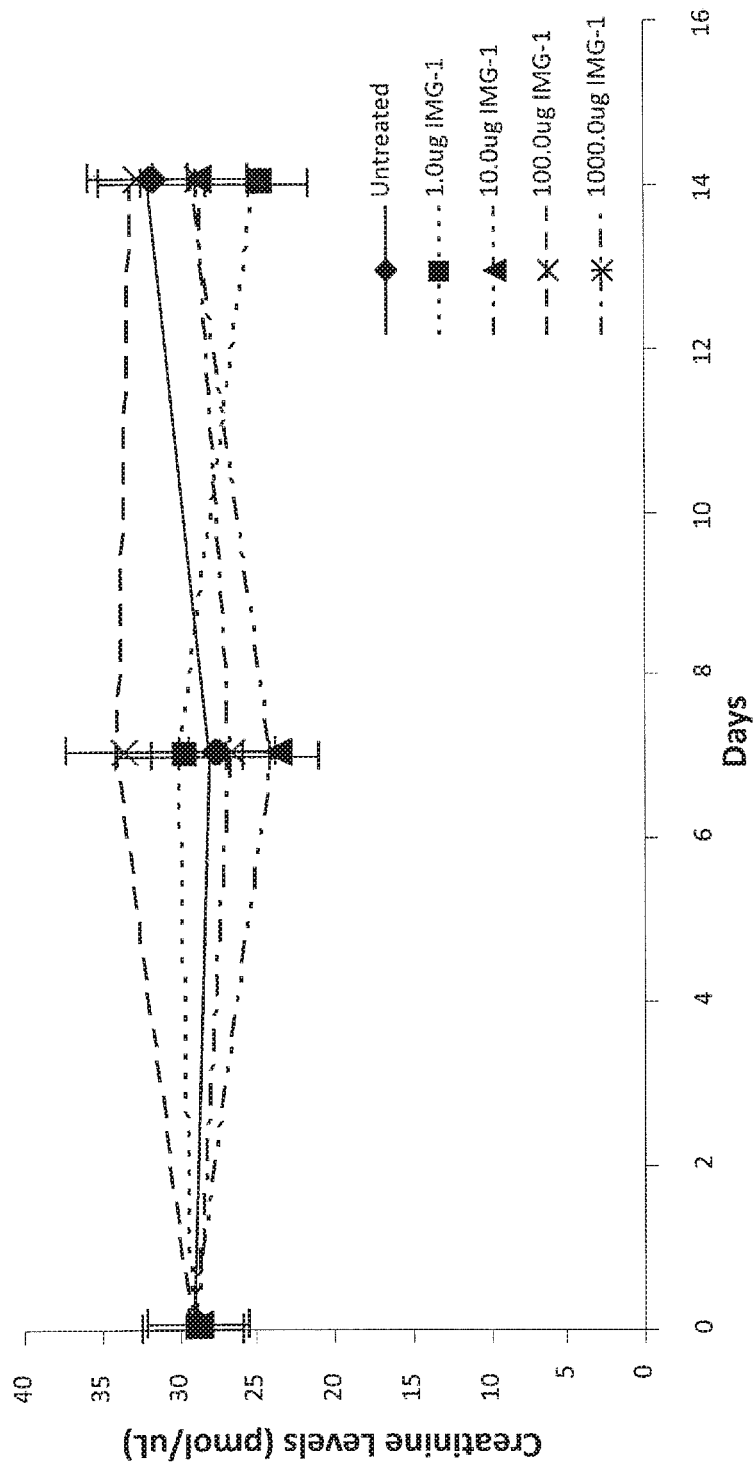
FIG. 11 is a graph showing that IMG-1 formulations administered at doses ranging from 1.0 µg to 1000.0 µg do not affect creatinine levels in Sprague Dawley rats.
Figure 12:
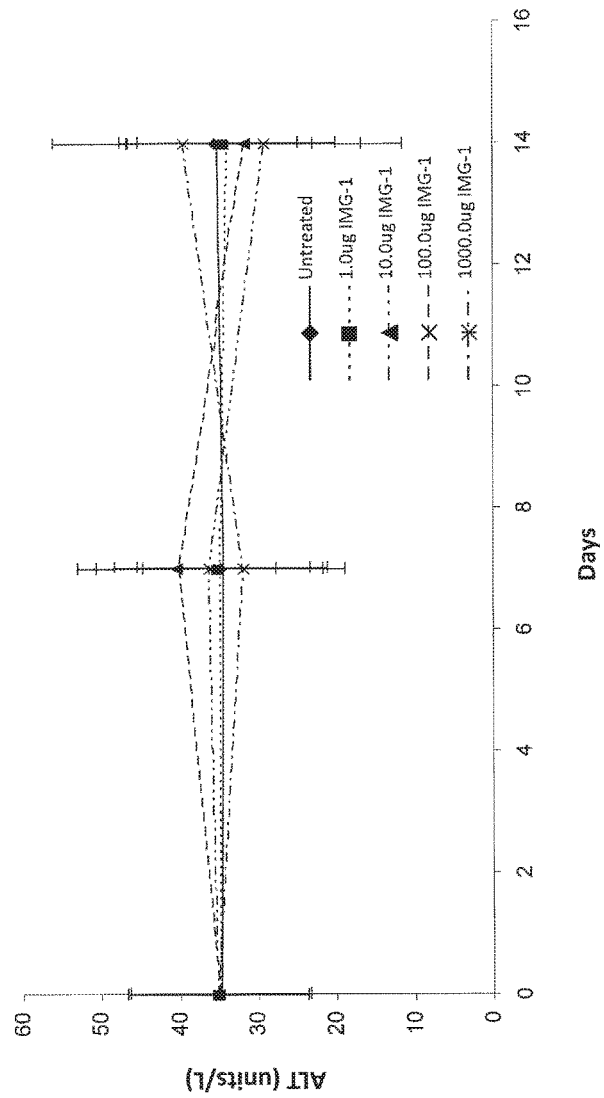
FIG. 12 is a graph showing that IMG-1 formulations administered at doses ranging from 1.0 µg to 1000.0 µg do not affect alanine aminotransferase levels in Sprague Dawley rats.

To assess toxicity of IMG-1 formulations, a Pilot Dose-Finding Toxicity Assay was performed with Sprague Dawley rats. The testing consisted of 5 groups, with 3 female and 3 male animals per group. Treated groups were given a single dose of one of the following IMG-1 concentrations: 1.0 µm, 10 µm, 100 µm or 1000 µg. A control group received no treatment. Clinical observations were performed every 1 hour for 4 hours post-dose administration, and daily for a total of 14 days for all 5 groups. Blood was drawn at 7 and 14 days post-administration for each of the 5 groups (treated and untreated). No adverse clinical observations were seen in any of the animals. Creatinine levels were measured to assess kidney function and alanine aminotransferase levels were measured to assess liver function in each of the 5 groups. No discernable differences between animals treated with IMG-1 formulation and untreated animals in both creatinine and alanine aminotransferase levels were seen, as shown in FIGS. 11 and 12, respectively.

Example 4: Insulin Clamp Study

The most widely accepted research method for quantifying insulin secretion and resistance is the euglycemic insulin clamp technique method, which measures either how well an animal metabolizes glucose or how sensitive an animal is to insulin. With this procedure, exogenous insulin is infused, so as to maintain a constant plasma insulin level above fasting, while glucose is fixed at a basal level, (between 100-150 mg/dl), by infusing glucose at varying rates.

Figure 13:
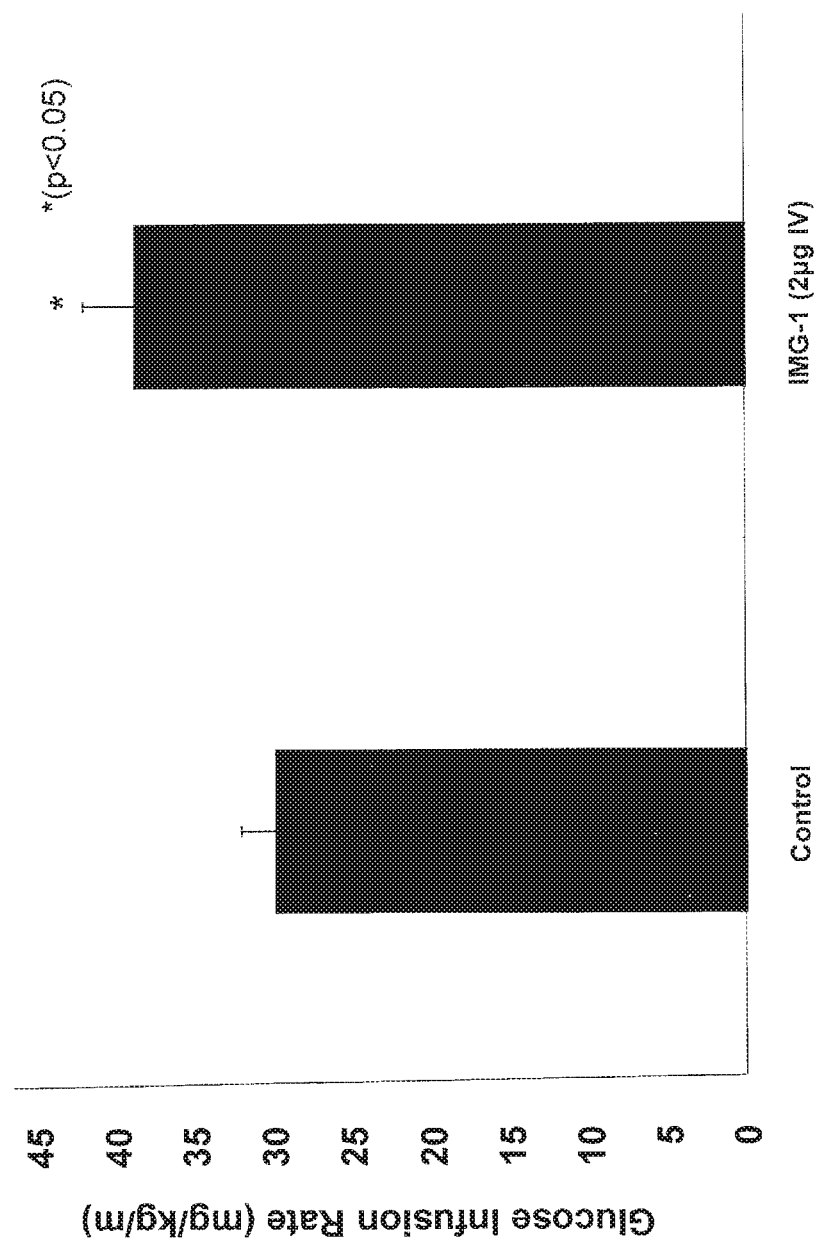
FIG. 13 is a bar graph showing that IMG-1 formulations administered at a dose of 2 µg (intravenous) decreases insulin resistance in Diabetic-Induced Obese (DIO) mice compared to control, based on glucose infusion rates (mg/kg/m).
Figure 14:
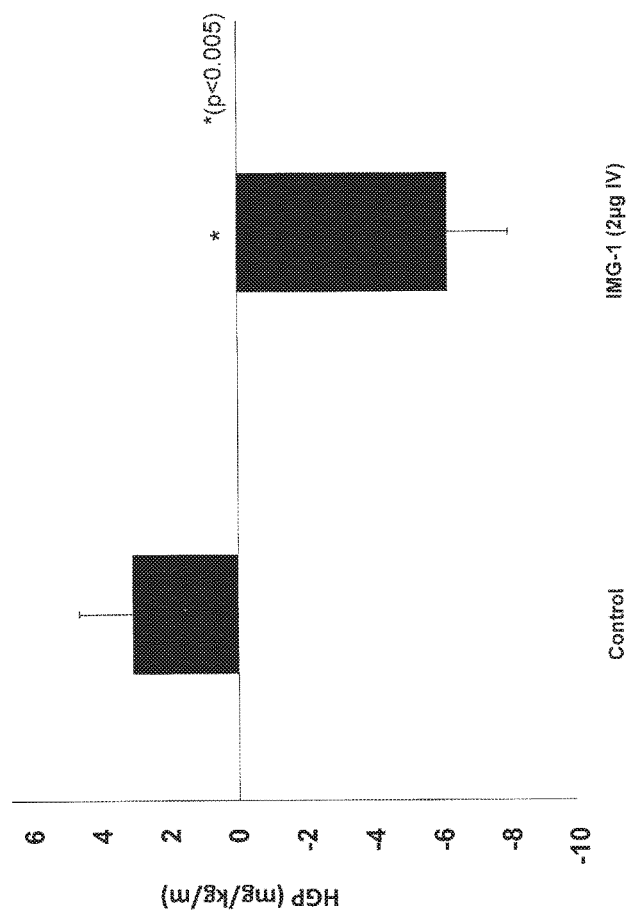
FIG. 14 is a bar graph showing that IMG-1 formulations administered at a dose of 2 µg (intravenous) inhibits hepatic glucose production (HGP) in DIO mice as compared to control.
Figure 15:
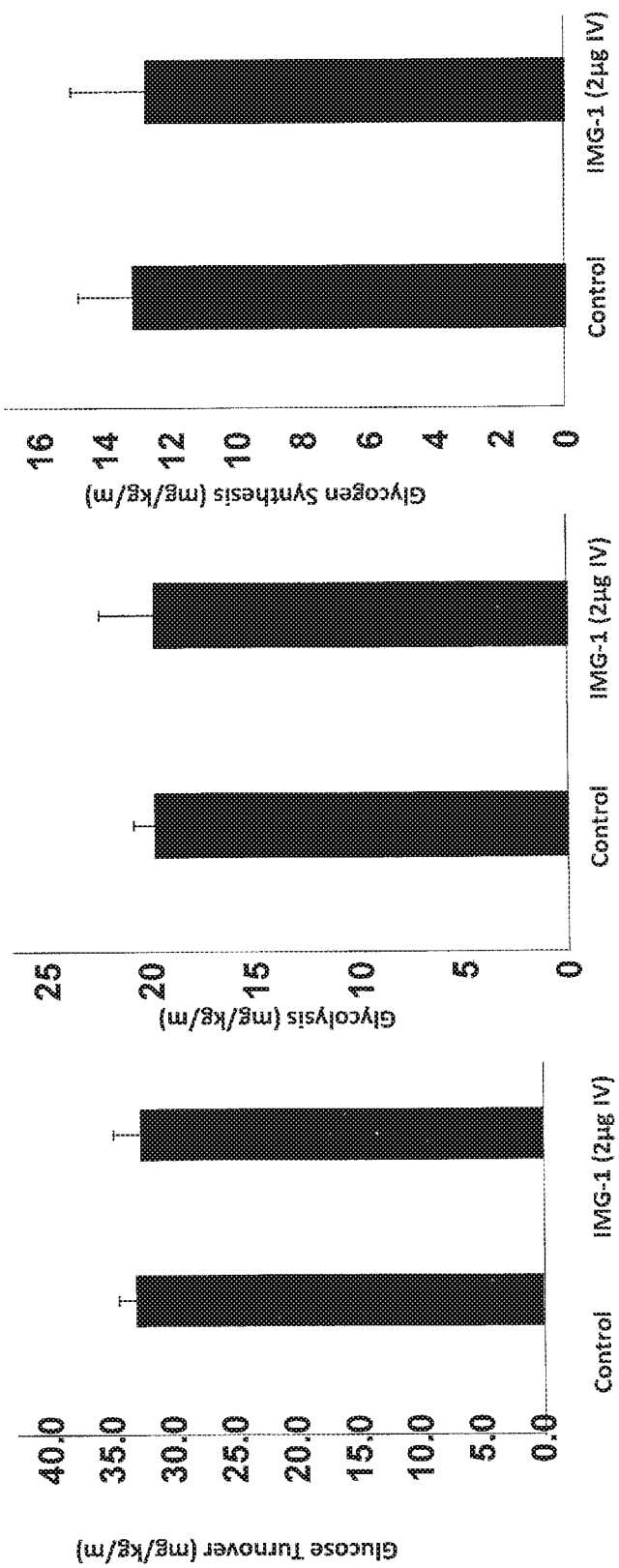
FIG. 15 is a bar graph showing that IMG-1 formulations at a dose of 2 µg (intravenous) do not affect whole body glucose turnover, glycolysis or glycogen synthesis in DIO mice and are essentially equivalent to control.
Figure 16:
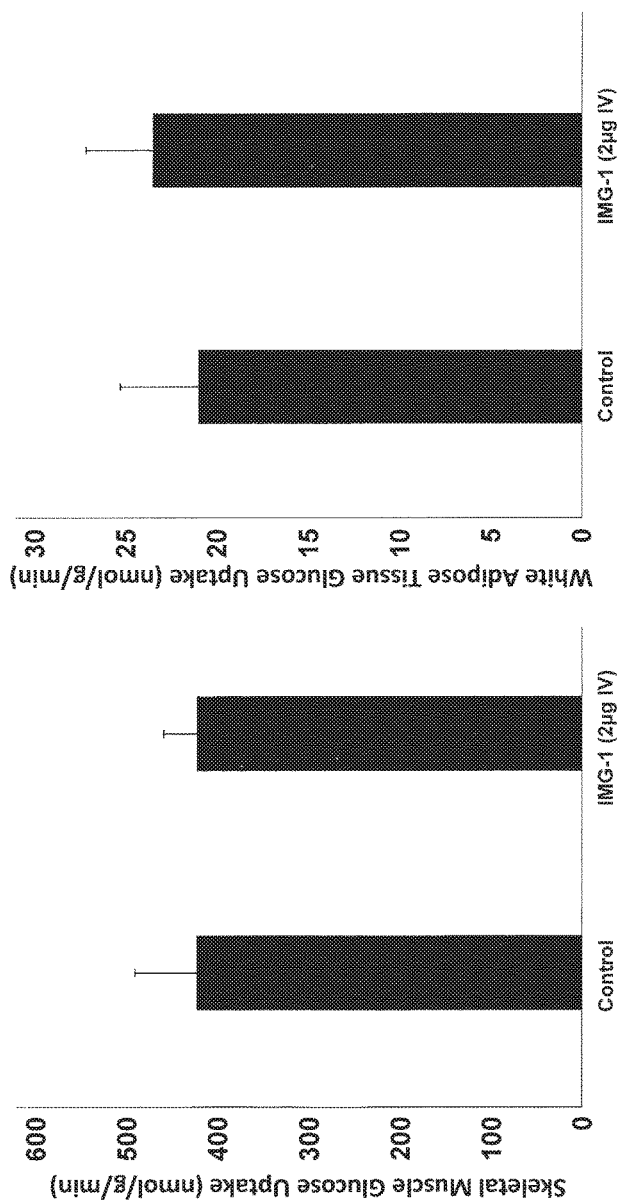
FIG. 16 is a bar graph showing that IMG-1 formulations at a dose of 2 µg (intravenous) do not affect skeletal muscle or white adipose glucose uptake.

To assess insulin action and glucose metabolism in IMG-1 treated animals (n=8) versus control (n=8), diet-Induced Obese (DIO) C57BL/6J mice underwent a 2-h hyperinsulinemic-euglycemic clamping procedure. Prior to clamping, a 2.mu.g IMG-1 formulation was administered (per animal) intravenously via tail veins at 48 hours and 24 hours prior to the clamp test, compared to PBS treated animals. IMG-1-treated animals had a significantly higher steady-state glucose infusion rates (38.8 mg/kg/mL) during clamping than PBS treated animals (30 mg/kg/mL). As shown in FIG. 13, treatment with IMG-1 decreases insulin resistance in DIO mice. Hepatic Glucose Production (HGP) was also dramatically suppressed in all animals treated with IMG-1, as shown by FIG. 14. Further, hepatic insulin action (the percent suppression of HGP) was increased in all IMG-1-treated animals during the hyperinsulinemic-euglycemic clamp. However, IMG-1 did not affect whole-body glucose turnover, glycolysis or glycogen synthesis in any of the treated animals, as evidenced by FIG. 15 showing the levels of glucose turnover, glycolysis and glycogen synthesis were nearly equal between the control animals and the treated animals. The results of the clamping procedure also showed that glucose metabolism in skeletal muscle and adipose tissue were not significantly different in either IMG-1 or PBS treated animals during the clamp assay, as evidenced by FIG. 16 which shows that skeletal muscle glucose uptake and white adipose tissue glucose uptake were nearly identical between the untreated and treated animals.

Example 5: Identification of RPS2 Active Regions

Full length purified RPS2 protein was digested with hydroxylamine (NH2OH), which cleaved RPS2 at two positions: amino acid 134 at Asn in position P1 and Gly in position P1', resulting in two subunits, designated RPS2-short (IMG-1 s) of approximately 13 kDa, and RPS2-long (IMG-1L) of approximately 18 kDa. The resulting fragments were resolved on a non-denaturing polyacrylamide gel, visualized and then electro eluted from the gel. The fragments were used to prepare formulations for testing in cell culture.

Figure 17:
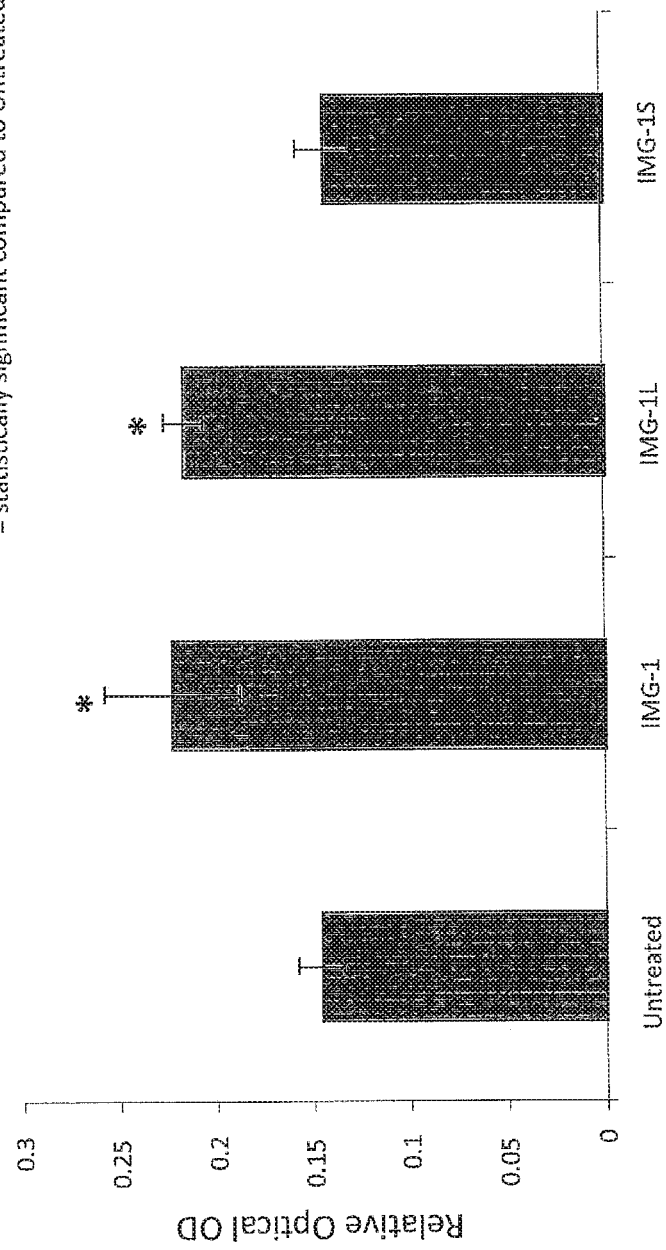
FIG. 17 is a bar graph showing the activity of truncated RPS2 peptides, designated as (IMG-1L and IMG-1S) compared to full-length RPS2 (IMG-1), and versus untreated. Formulations of IMG-1L, which correspond to fragments of the C-terminus of the full-length protein, exhibited similar activity in vitro compared to IMG-1 (full length); whereas, formulations of IMG-1S (corresponding to the fragment of the N-terminus of the full-length protein) did not appear to exhibit activity, as measured by Optical Density from an MTT assay using endothelial cells.

Human Dermal Microvascular Endothelial Cells (CADMEC/HMVEC) provide an excellent model system to study many aspects of endothelial function and disease, especially those related to the microvasculature. The MU assay is a colorimetric assay for assessing cell metabolic activity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. In order to assess the effect of IMG formulations on cellular activity, CADMEC cultures, such as those available from Cell Applications, Inc., were treated with one of the various formulations: 0.5 µg/mL full length protein (designated IMG-1), 0.5 µg/mL of C-terminal fragment (designated IMG-1L), or 0.5 µg/mL of N-terminal fragment (designated IMG-1 s). The treated cultures were allowed to grow for 72 h. Following 72 h of cell growth, 100 µL of cell cultures were treated with 10 µL of 12 mM MU, and incubated at 37° C. for 4 hours. Following the 4 h incubation with MTT, 100 µL of an SDS-HCl solution was added to the MU-treated cell cultures, in order to solubilize the crystals, and was further incubated for an additional 4 hrs. Absorbance was then read at 570 nm using a Microplate Absorbance Spectrophotometer (similar to the xMark™ from BioRad). As shown in FIG. 17, at 72 h there was a significant increase in relative optical OD in cells treated with formulations of IMG-1 and IMG-1L (164% and 157% respectively), while IMG-1S did not appear to affect cell growth and untreated levels were in line with IMG-1S formulations. IMG-1L correspond to fragments of the C-terminus of the full-length protein; whereas, formulations of IMG-1S correspond to the fragment of the N-terminus of the full-length protein. Thus, the C-terminus of RPS2 and fragments and/or analogues thereof are of therapeutic value, along with the full length RPS2 protein.

Example 6

Similar conditions are described by Examples 1 and 2 were carried out to test SEQ ID. No 2 as a therapeutic for the treatment of diabetes, hypertension and hypercholesterolemia.

Figure 18:
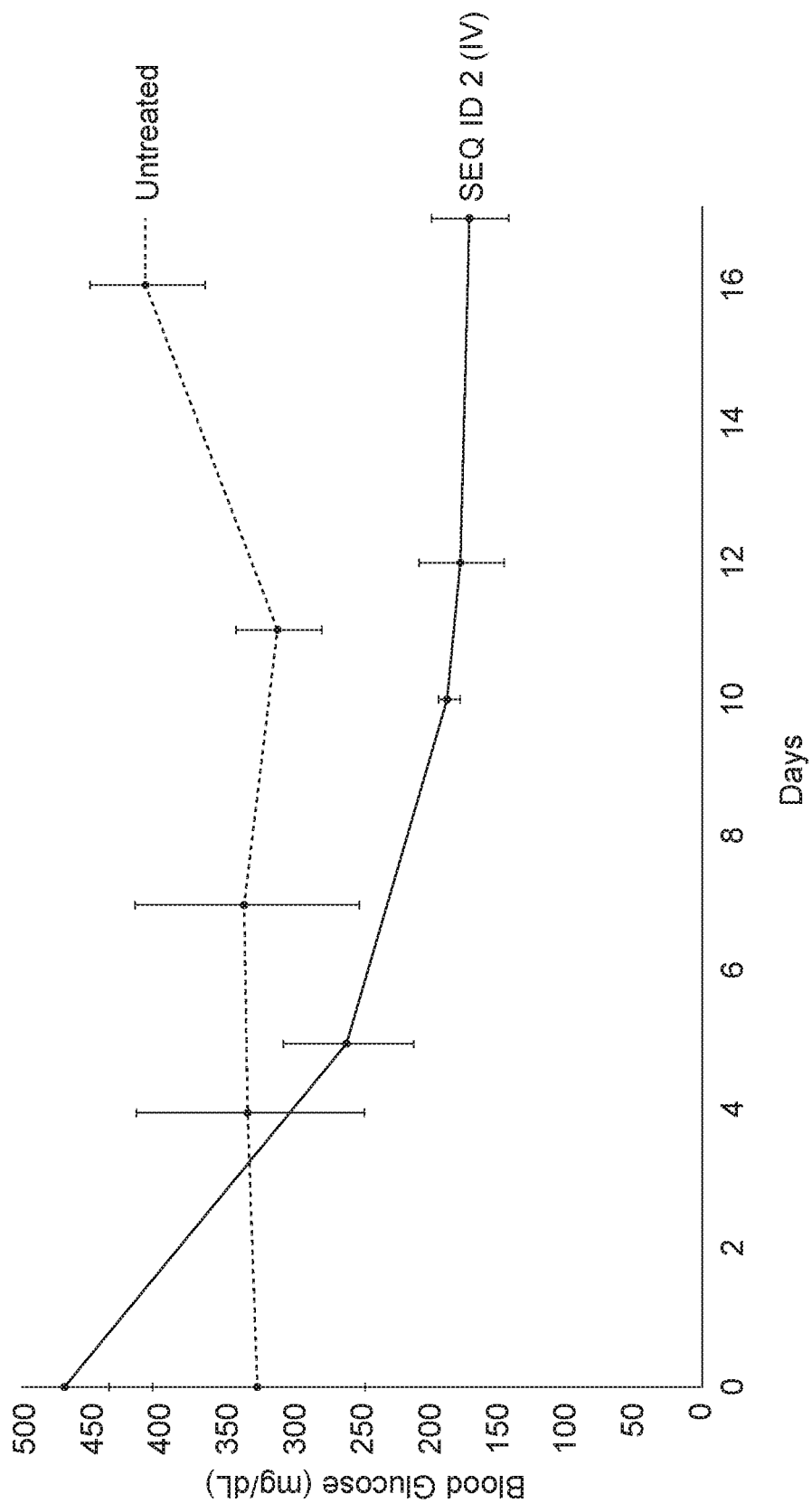
FIG. 18 (as a supplement to FIG. 2) shows that SEQ ID No. 2 has therapeutic benefits comparable to SEQ ID No. 1; treatment with compositions comprising SEQ ID No. 2 (IM2) normalize blood glucose levels in the diabetic animal model, compared to age/species/time matched controls.

As described, Zucker Diabetic Fatty (ZDF) rats were fed a special diet of Purina 5008 (Charles River Laboratories International, Inc.) to increase their body weight. Prior to the study the animals blood glucose levels were assessed; only rats who had blood glucose levels greater than 200 mg/dl were used in the study. The animals were treated with 10 µg once-daily composition comprising SEQ ID No. 2 (also referred to as IMG-2, and corresponding to IMG-L) intravenously (IV, n=2). Fasting blood glucose (FBG) levels were assessed in the ZDF throughout the experiment using an Accutrend Plus System. The ZDF rats treated with the composition comprising SEQ ID No. 2 showed a marked decrease in blood glucose levels, (average FBG levels of 260 mg/dl vs a starting FBG levels of 469 mg/dl), within 5 days; all animals treated with compositions comprising SEQ ID No. 2 exhibited normal FBG levels (levels below 200 mg/dl) by day 10. FIG. 18 shows that SEQ ID No. 2 has therapeutic benefits by normalizing blood glucose levels in the diabetic animal model, compared to historical age/species/time matched controls.

Figure 19:
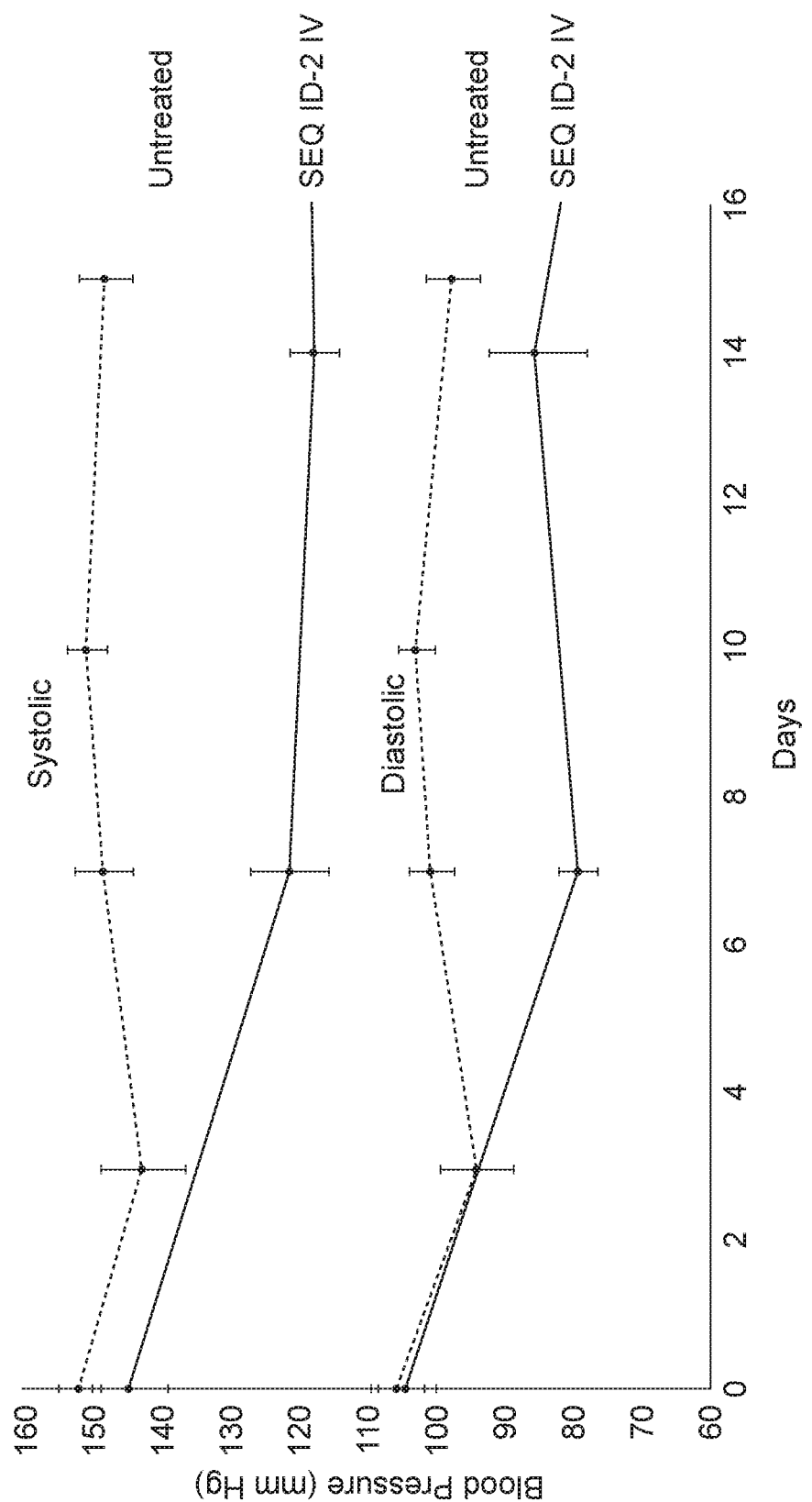
FIG. 19 systolic and diastolic blood pressure levels in animals treated with IMG-2 compared to age/species/time matched controls as a supplement to FIG. 3; the IMG-2 treated animals had significantly decreased levels of cholesterol compared to the untreated cohort.

The blood pressure of the ZDF rats also was monitored weekly using a tail cuff blood pressure monitor (CODA, Monitor from Kent Scientific). Within 7 days of treatment rats treated with IMG-2 started exhibiting normal blood pressure (144/122 mmHg on day 0 vs 121/79 mmHg on day 7). FIG. 19 shows systolic and diastolic blood pressure levels in animals treated with IMG-2 compared to historical age/species/time matched controls.

Figure 20:
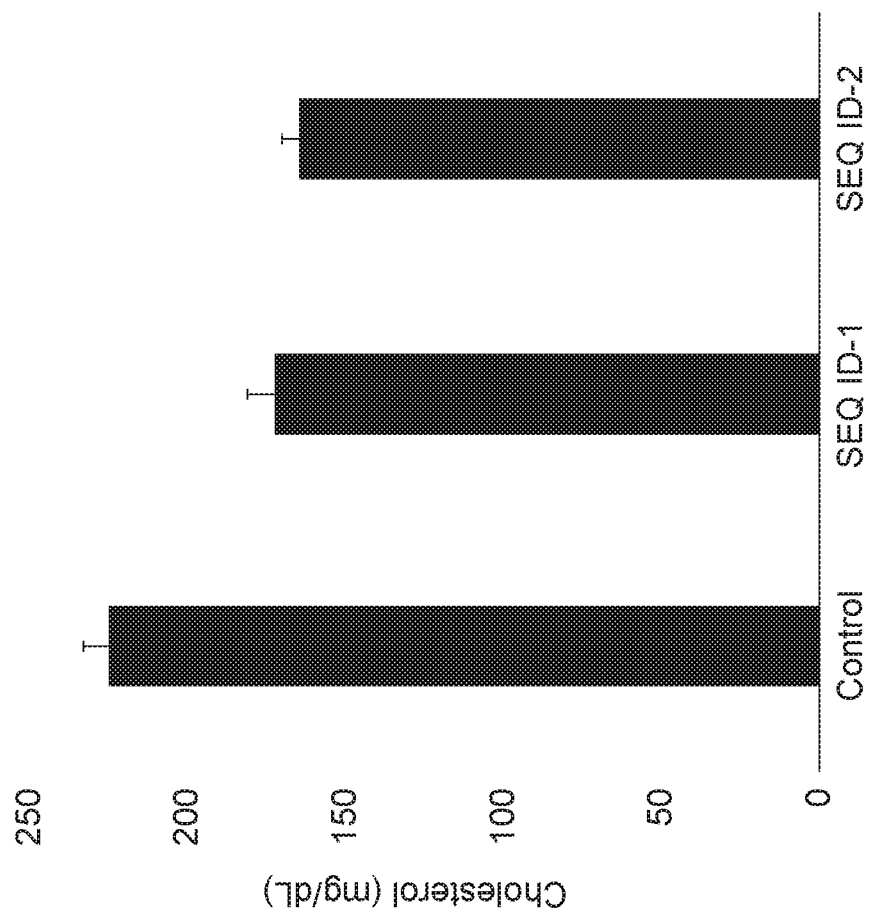
FIG. 20 shows that compositions comprising IMG-2 caused a decrease in cholesterol levels in the diabetic animal model comparable as seen with the treatment of the same animal model with IMG-1 (compositions comprising SEQ ID No. 1), compared to untreated ZDF rats (supplement to FIG. 7).

The cholesterol levels of the ZDF rats were also assessed following treatment with 20 µg IMG-2 (n=2). The IMG-2 treated animals had significantly decreased levels of cholesterol compared to the untreated cohort. FIG. 20 shows that compositions comprising 20 µg SEQ ID No. 2 (IMG-2) caused a decrease in cholesterol levels in the diabetic animal model comparable as seen with the treatment of the same animal model with IMG-1 (compositions comprising SEQ ID No. 1), compared to untreated ZDF rats; the untreated animals had a cholesterol level of 224 mg/dL, while IMG-1 treated animals had cholesterol levels of 171 mg/dL, and IMG-2 treated animals had an average cholesterol level of 164 mg/dL.

Exemplary IMG-1 Formulations

The present invention provides pharmaceutical compositions comprising one or more of a polypeptide, peptide, and/or analogue corresponding to one more of SEQ ID NO: 1, SEQ ID NO: 2, SEQ ID NO:3 and/or SEQ ID NO:4.

Formulations of the present invention comprising a purified or synthetic peptide or peptide analogue corresponding to SEQ ID: 01, SEQ 1 NO: 2, SEQ ID NO:3, and/or SEQ ID NO: 4 may be formulated according to methods available to one of ordinary skill in the art. In one embodiment, a pharmaceutical formulation comprises an RPS2 polypeptide or analogue, or an active peptide region thereof, corresponding to one of SEQ ID NO(s) 1-4, in a range of less than 20 µg and up to 150 µg, as a solid dose form or a solution. In one embodiment, formulations comprise the peptide present at a concentration of 0.05 to 5 µg/L; in another embodiment formulations comprise peptide present at a concentration of 0.1 to 1 µg/L; in yet another embodiment, formulations comprise peptide present at a concentration of 50-150 µg/kg for an oral formulation and 5-15 µg/kg for an intravenous formulation. Concentration of active ingredient and corresponding dosage will depend, in part, on the weight of the subject, the route of administration, the symptoms/disorder to be treated, and the severity of the symptoms.

In one embodiment, a pharmaceutical formulation of the present invention further comprises one or more absorption enhancers, including one or more of detergents, surfactants, bile salts, $Ca^{2+}$ chelating agents, fatty acids, medium chain glycerides, acyl carnitine, alkanoyl cholines, N-acetylated α-amino acids, N-acetylated non-α-amino acids, chitosans, mucoadhesive polymers, and phospholipids.

In one embodiment, exemplary excipients useful for the present invention include: buffers, salts, surfactants, polyol/disaccharide/polysaccharides, amino acids, and antioxidants. Exemplary buffers that keep pH levels between 4.7 and 7.4 include: acetate, citrate, histidine, succinate, phosphate, and hydroxymethylaminomethane (Tris). Exemplary surfactants include: polysorbate 80 (Tween 80), polysorbate 20 (Tween 20), and poloxamer 188. Lyophilized (freeze-dried) formulations may use one or a mixture of polyol/disaccharide/polysaccharide (e.g., mannitol, sorbitol, sucrose, trehalose, and dextran 40). Sugars provide bulk for lyophilized formulations and are known to serve as stabilizing agents for therapeutic proteins. Sodium chloride (NaCl) is commonly used with protein formulations. Exemplary antioxidants include ascorbic acid, methionine, and ethylenediaminetetraacetic acid (EDTA).

In another embodiment, a pharmaceutical formulation of the present invention further comprises a surface modification by one or more lipophilic moieties. In yet another embodiment, a pharmaceutical formulation comprises active agent optionally co-administered with concentrated solution of one or more carrier molecules.

In yet another embodiment, a pharmaceutical formulation further comprises one or more synthetic bio adhesive polymers comprising polyacrylic acid or cellulose derivatives. Examples of polyacrylic acid-based polymers include, but are not limited to, carbopol, polycarbophil, polyacrylic acid (PAAc), polyacrylate, poly (methylvinylether-co-methacrylic acid), poly (2-hydroxyethyl methacrylate), poly (methacrylate), poly(alkylcyanoacrylate), poly(isohexylcyanoacrylate) and poly(isobutylcyanoacrylate). Cellulose derivatives include, but are not limited to, carboxymethyl cellulose, hydroxyethyl cellulose, hydroxypropyl cellulose, sodium carboxymethyl cellulose, methylcellulose, and methylhydroxyethyl cellulose. In addition, seminatural bioadhesive polymers include chitosan and various gums such as guar, xanthan, poly(vinylpyrrolidone), and poly(vinyl alcohol).

In yet another embodiment, a pharmaceutical formulation of the present invention further comprises a gastrointestinal mucoadhesive patch system (GI-MAPS) comprising active agent with layered films contained in an enteric capsule, with a backing layer comprising a water-insoluble polymer, ethyl cellulose (EC); a surface layer comprising an enteric pH-sensitive polymer such as hydroxypropylmethylcellulose phthalate, Eudragit L100 or S100; a coating layer comprising an adhesive layer; and a middle layer, peptide-containing layer, made of cellulose membrane attached to the backing layer. After oral administration, the surface layer dissolves at the targeted intestinal site and adheres to the small intestinal wall, where a closed space is created on the target site of the gastrointestinal mucosa by adhering to the mucosal membrane. As a result, both the active agent and the absorption enhancer coexist in the closed space and a high-concentration gradient is formed between inside the system and the enterocytes, which contributes to enhanced absorption of peptide.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A pharmaceutical composition comprising a therapeutically effective amount of a polypeptide consisting of the amino acid sequence according to SEQ ID NO:2, wherein the therapeutically effective amount is sufficient to lower blood glucose level in a subject to less than 200 mg/dL.

2. The pharmaceutical composition of claim 1, wherein the composition is suitable for oral or parenteral administration.

3. The pharmaceutical composition of claim 1, further comprising one or more of a pharmaceutically acceptable carrier, a pharmaceutically acceptable diluent, and/or one or more of a pharmaceutically acceptable excipient.

4. The pharmaceutical composition of claim 1, wherein the composition is a treatment for one or more of diabetes, hyperglycemia, and hypertension when administered to a subject in need thereof.

* * * * *

```
                        SEQUENCE LISTING

<160> NUMBER OF SEQ ID NOS: 1

<210> SEQ ID NO 1
<211> LENGTH: 159
<212> TYPE: PRT
<213> ORGANISM: Homo sapiens

<400> SEQUENCE: 1

Gly His Val Gly Leu Gly Val Lys Cys Ser Lys Glu Val Ala Thr Ala
1               5                   10                  15

Ile Arg Gly Ala Ile Ile Leu Ala Lys Leu Ser Ile Val Pro Val Arg
            20                  25                  30

Arg Gly Tyr Trp Gly Asn Lys Ile Gly Lys Pro His Thr Val Pro Cys
        35                  40                  45

Lys Val Thr Gly Arg Cys Gly Ser Val Leu Val Arg Leu Ile Pro Ala
    50                  55                  60

Pro Arg Gly Thr Gly Ile Val Ser Ala Pro Val Pro Lys Lys Leu Leu
65                  70                  75                  80

Met Met Ala Gly Ile Asp Asp Cys Tyr Thr Ser Ala Arg Gly Cys Thr
                85                  90                  95

Ala Thr Leu Gly Asn Phe Ala Lys Ala Thr Phe Asp Ala Ile Ser Lys
            100                 105                 110

Thr Tyr Ser Tyr Leu Thr Pro Asp Leu Trp Lys Glu Thr Val Phe Thr
        115                 120                 125

Lys Ser Pro Tyr Gln Glu Phe Thr Asp His Leu Val Lys Thr His Thr
    130                 135                 140

Arg Val Ser Val Gln Arg Thr Gln Ala Pro Ala Val Ala Thr Thr
145                 150                 155
```